(12) United States Patent
Matos

(10) Patent No.: US 8,473,065 B2
(45) Date of Patent: Jun. 25, 2013

(54) IMPLANTABLE MEDICAL DEVICE WHICH MAY BE CONTROLLED FROM CENTRAL STATION

(76) Inventor: Jeffrey A. Matos, New Rochelle, NY (US)

( * ) Notice: Subject to any disclaimer, the term of this patent is extended or adjusted under 35 U.S.C. 154(b) by 1208 days.

(21) Appl. No.: 12/154,079

(22) Filed: May 19, 2008

(65) Prior Publication Data

US 2008/0300659 A1 Dec. 4, 2008

Related U.S. Application Data

(60) Provisional application No. 60/930,525, filed on May 17, 2007.

(51) Int. Cl.
*A61N 1/00* (2006.01)
(52) U.S. Cl.
USPC ............................................. 607/60
(58) Field of Classification Search
USPC ........... 128/200.16, 200.14, 899; 340/539.17, 340/870, 1; 600/300, 484, 509; 607/4, 14, 607/18, 30, 31, 60
See application file for complete search history.

(56) References Cited

U.S. PATENT DOCUMENTS

| 2001/0031997 | A1* | 10/2001 | Lee ................................ 607/59 |
| 2002/0052539 | A1* | 5/2002 | Haller et al. ................... 600/300 |
| 2005/0115561 | A1* | 6/2005 | Stahmann et al. ....... 128/200.24 |
| 2007/0162081 | A1* | 7/2007 | Yu et al. .......................... 607/18 |

* cited by examiner

*Primary Examiner* — George Manuel
*Assistant Examiner* — Robert N Wieland
(74) *Attorney, Agent, or Firm* — Eckert Seamans Cherin & Mellott, LLC

(57) ABSTRACT

An implantable medical device (IMD) comprises a transmitting/receiving (T/R) device for transmitting medical data sensed from a patient to, and for receiving control signals from, a medical expert (a human medical professional and/or a computerized expert system) at a remote location; an electronic medical treatment device for treating the patient in response to control signals applied thereto; and a sensor circuit, having a sensor circuit output, for producing sensor circuit output signal(s) representing medical data sensed from the patient. The IMD also includes logic device which analyzes the sensor circuit output signal(s) to detect a medical abnormality and either sends a notification signal as well as signal(s) representing a medical state of said patient to the medical expert at the remote location or sends a local treatment device control signal to the medical treatment device, or does both.

123 Claims, 20 Drawing Sheets

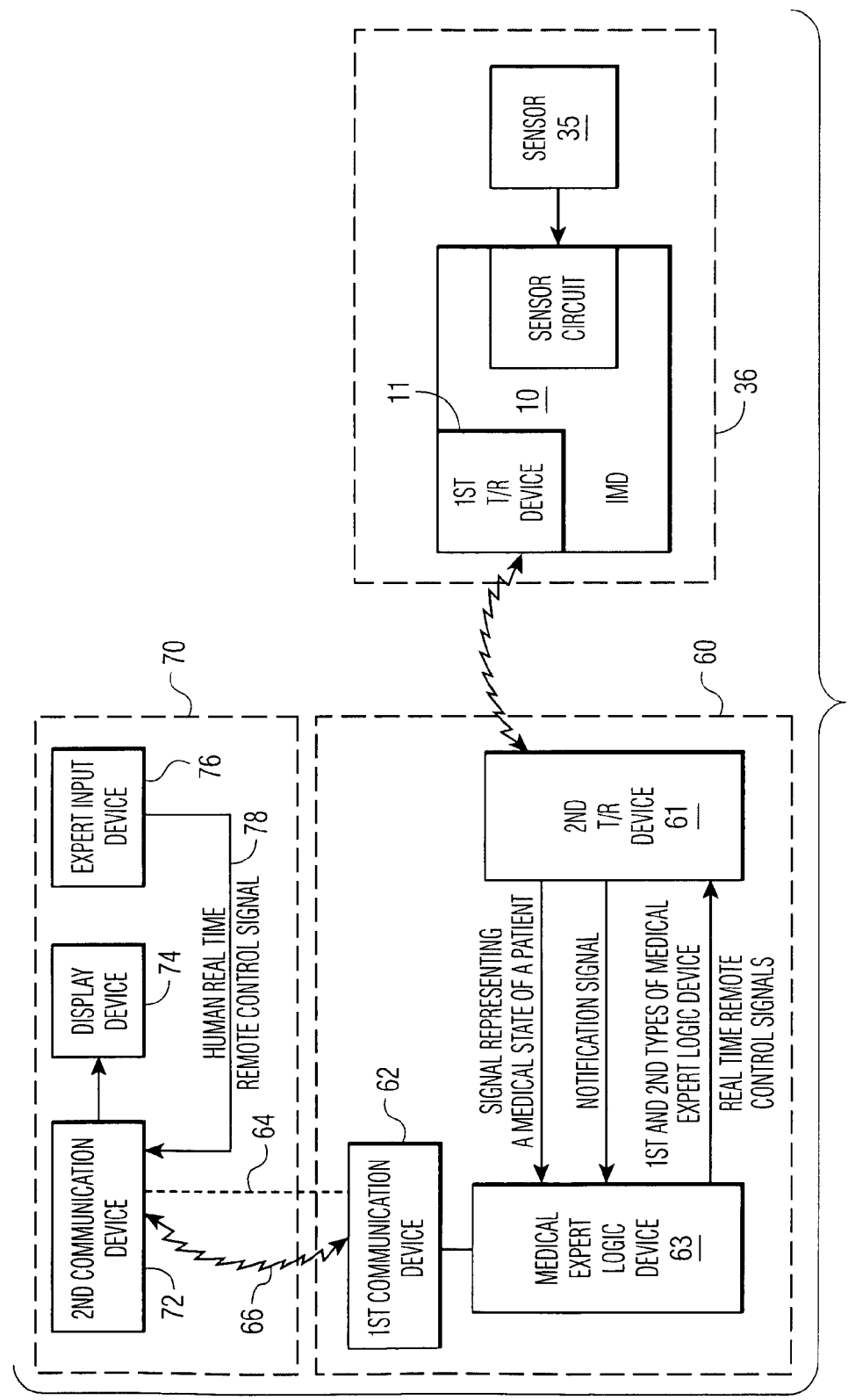

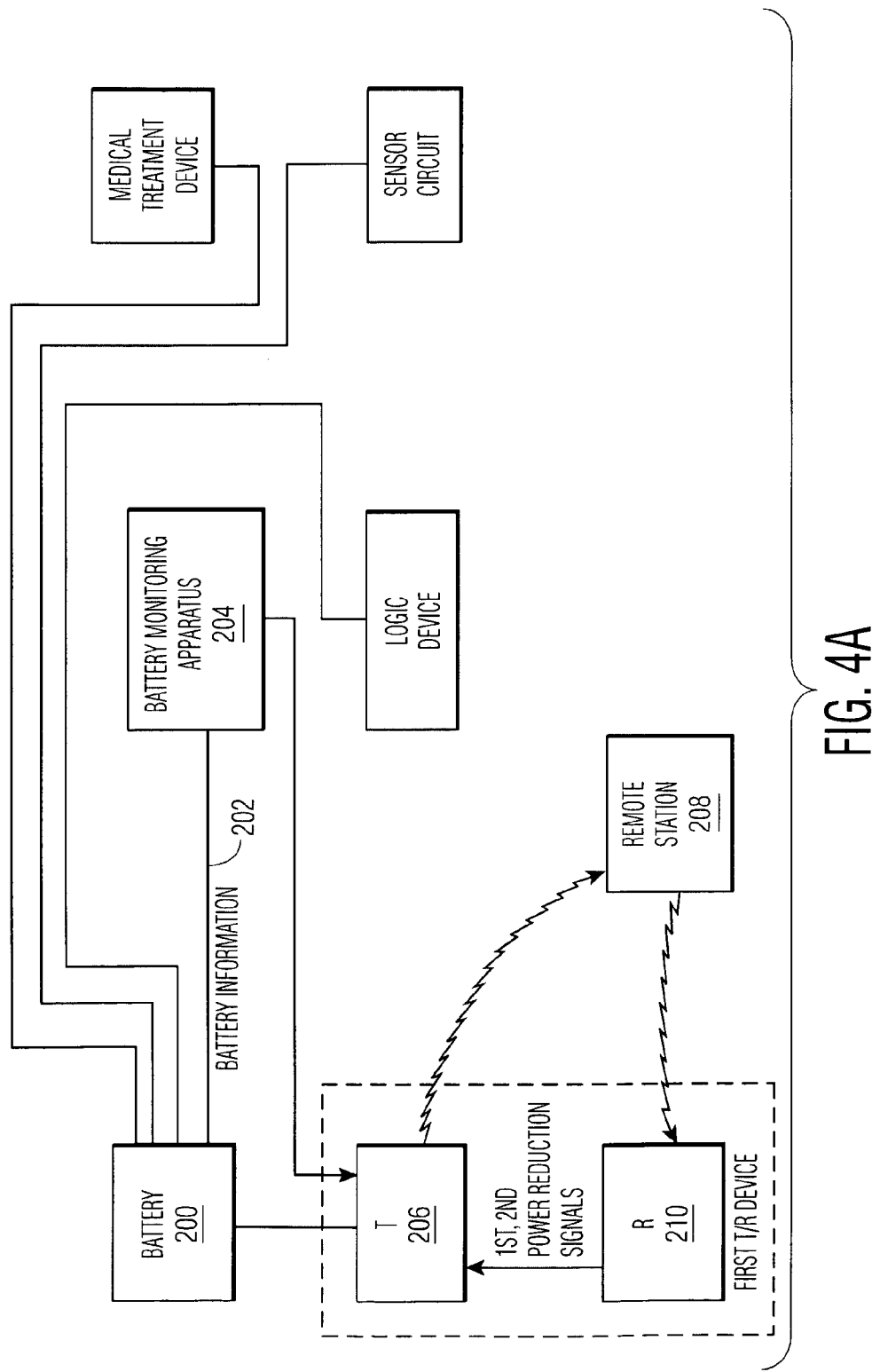

IMPLANTABLE MEDICAL DEVICE WHICH MAY BE CONTROLLED FROM CENTRAL STATION

CROSS REFERENCE TO RELATED PATENTS AND APPLICATIONS

This application claims priority from Provisional Application No. 60/930,525 filed May 17, 2007.

The subject matter of this application is related to that of U.S. patent application Ser. No. 10/460,458, now U.S. Pat. No. 7,277,752, and U.S. patent application Ser. No. 11/502,484 which are incorporated herein by reference.

BACKGROUND OF THE INVENTION

An early generation of implantable cardioverter-defibrillators, "ICDs" had one programmable function: on and off. The modern version of the device has dozens of programmable parameters. In fact, it is now not uncommon for physicians who regularly use such devices to not be fully versed in all of the possible programming complexities of the devices that they implant. Furthermore, the optimal value of some programmable parameters can not be know at the time of device implantation. Physicians will not uncommonly guess at the values to be programmed for anti-tachycardia pacing, because they may not be able to accurately reproduce the tachycardia that a patient may later have. It is therefore not uncommon for physicians to reprogram such parameters, weeks, months or years later, after the occurrence of the actual event showed that they had not guessed well. Occasionally, the examples are striking. A patient, for example with an ICD and both ventricular tachycardia and atrial fibrillation may get not just one but quite a few inappropriate defibrillator shocks, because of an inappropriately selected programmed rate cutoff, stability parameter, etc. The opposite sort of phenomenon may also occur. For example, a patient with known ventricular tachycardia, "VT", at 200 beats per minute, "bpm", may have the VT detect rate of an ICD programmed to 180, and may later collapse because of an unexpected episode of VT below the rate cutoff.

Occasionally, the malfunctioning of an implanted device can have very serious consequences. The Ventritex V-110 defibrillator at one point had a failure mode which resulted in the sudden death of at least one patient. The "fix" for it, was a programming fix, wherein the downloading of certain instructions prevented the device from being subject to this malfunction.

The explosive growth of modern communication systems allows for the possibility of remote supervision and management of implantable devices, and addressing of the aforementioned problems. An ICD which may be providing numerous inappropriate shocks over a short time period—either due to device malfunction, lead malfunction or inappropriate programming of a properly functioning system, could be remotely identified and reprogrammed, for example.

A variety of other devices which perform critical functions which remote control could enhance. These include cardiac pumps, insulin pumps, brain stimulating devices and others.

There are certain requirements that must be fulfilled if some of the autonomy of device function is to be impinged on. Remote control over a faulty communication link could create problems instead of solving them, so reliability of communications, careful communication monitoring, redundancy and contingency planning, are all features of a remotely controllable implantable device. Since the communication process uses battery power, judicious power management is also a necessity.

SUMMARY OF THE INVENTION

Hereinbelow: Medical Expert, "ME", refers to either a person (a "medical professional") or an expert computational system.

The inventions disclosed herein concern methods and apparatus for remotely controlling implantable medical devices such as ICDs, pacemakers, drug infusion pumps, brain stimulators etc. In order to conserve battery power, the communication link between the device and a medical expert is designed to function only when needed. Such need is defined by preprogramming certain notification criteria, such that the device initiates communication with a ME only when the assistance of that ME may be needed. Following notification the ME may observe the sensor information that the device observes in making a device management decision. Furthermore, the ME may have access to additional information e.g. historical information within the device memory, historical information about the particular patient from one or more accessible databases, and information about a plurality of patients with the device from still other databases. The ME may have a variety of control-sharing relationships with the implanted device ranging from complete control (with simultaneous complete inhibition of internal control circuits), or a sharing arrangement in which, for example, both the ME and the control circuits of the IMD may be able to influence treatment. Following such an encounter, the ME may modify the device functioning by reprogramming a number of parameters (e.g. notification parameters, a value of one or more parameters which define a threshold for treatment, the actual treatment parameters, battery management, and the nature of the control-sharing arrangement for future episodes involving notification).

BRIEF DESCRIPTION OF THE DRAWINGS

FIG. 2C is a representational block diagram of a system including an IMD, a sensor and a remote station operated by a computational device and a further remote station operated by a human medical expert.

FIG. 4A is a representational block diagram showing remotely controlled power management for a remotely controllable IMD with one battery.

DETAILED DESCRIPTION OF THE PREFERRED EMBODIMENTS

Figure 1:
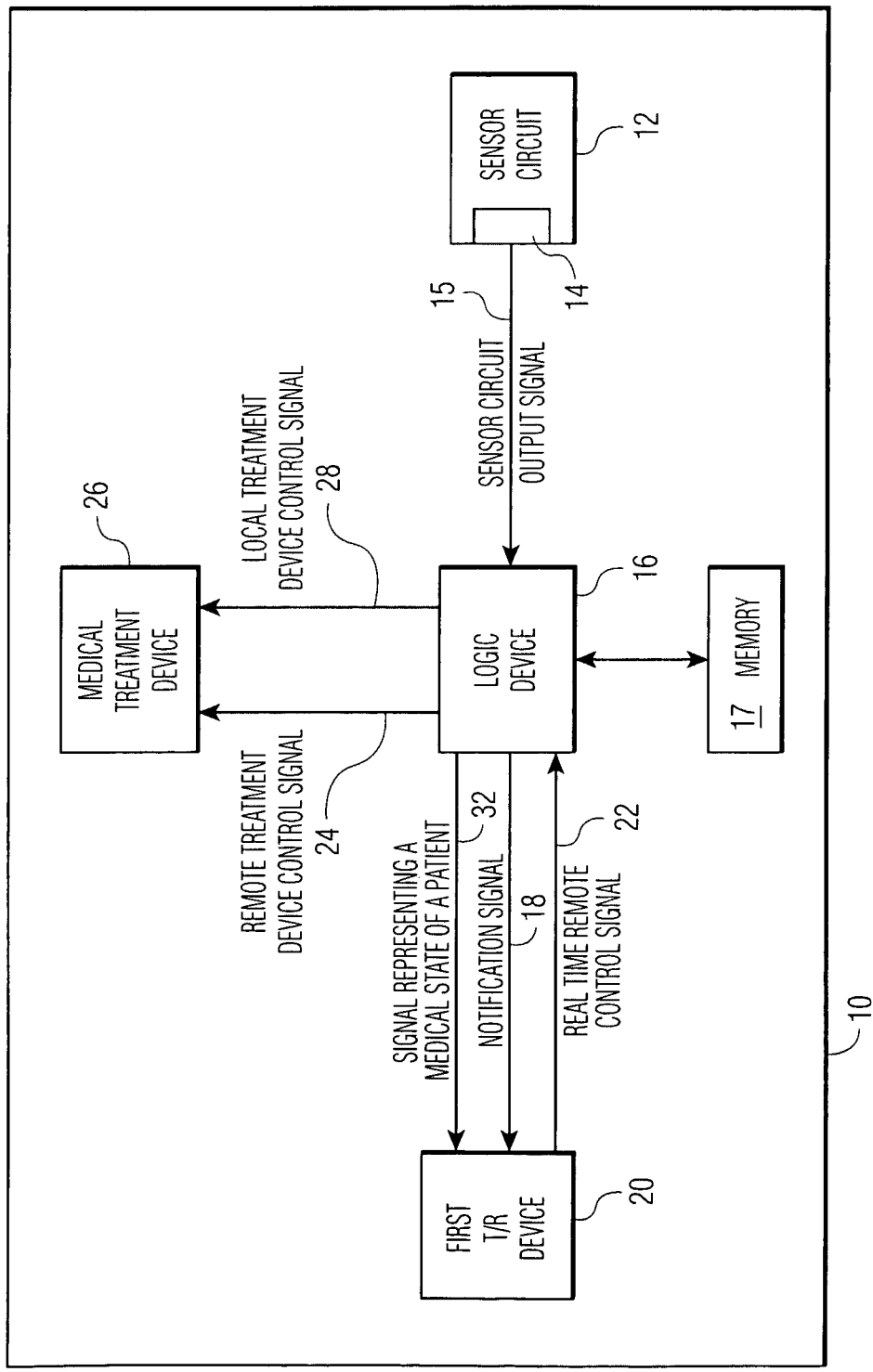
FIG. 1 is a representational block diagram of an implantable medical device ("IMD") which may be remotely controlled.

FIG. 1 shows an implantable medical device 10 which has the capacity to notify a remotely located medical expert. Sensor circuit 12, with output 14, outputs sensor circuit output signals 15. The signals contain data regarding the measurement of at least one medical parameter, a parameter which allows the logic device 16 of the IMD to make treatment decisions. 15 may be an analog signal or a digitized one, as is known in the art. Means for amplification, of 15 and other techniques for signal management as are known in the art, may reside within 12. The sensor circuit is coupled to a sensor, as discussed hereinbelow.

Logic device 16 analyzes signals 15 to determine if there is a need for (a) treatment of a medical abnormality, and/or (b) notification of a remotely located medical expert. Scenarios are possible in which:
1) the abnormality which calls for notification is the same as that which call for treatment;
2) the abnormality which calls for notification is less severe than that which requires treatment;
3) the abnormality which calls for notification is more severe than that which requires treatment; and
4) the abnormality which calls for notification is different than that which requires treatment.

By way of example: In the case of 2) and 4) hereinabove, there may be abnormalities which, though not severe enough to always require treatment, might require treatment under certain circumstances which are apparent to an expert person or system. Thus, providing an ICD shock for VT with a rate of over 240 bpm would be likely to represent sound management much of the time, but the desirability of providing an ICD shock for VT at 140 bpm will depend on a variety of circumstances. Some of these may be easily programmed, such as the duration of the event VT. But others may not. If the ICD in the example was connected to multiple sensors, then a complex decision based on the patient's blood pressure, respiratory rate, and even recent medical history and/or response to antitachycardia pacing in the past might all be factors that would be advisably considered in making a shock/no shock decision. In the case of therapy decision making based on multiple sensors, it becomes impossible to simply say that on set of abnormalities is more severe than another, and "different" is the appropriate term. Thus a VT rate of 140 and a blood pressure of 80 systolic may or may not be considered more severe than a situation with VT at 240 and a blood pressure of 90. Clearly, as the number of different types of sensors increases, and treatment decisions must be based on the data from each of them, algorithms will be more difficult to design, and there will be decreasing likelihood that such algorithms can match the decision making ability of a medical expert, "ME" (person or computational system). The value of having the device "seek consultation" with a ME under these circumstances is clear. At times, the blending of information from multiple sensors may be best accomplished using mathematical techniques which are beyond the scope of a routinely implanted device. Ultimately, treatment decisions may be based on complex functions of multiple parameters and time. Note is made of the fact that these functions may not meet all of the formal mathematical criteria of a function, since input data may not be continuous in nature.

By way of yet another example: It may be desirable to notify and ME only in cases of extreme abnormality, and to omit such notification for routine treatments. In such a circumstance, 16 could be operative to treat non-severe abnormalities without notification and to notify a ME for very severe ones. It could be further operative to treat the severe ones unless, having been notified of a severe event, a ME chooses to override the decision of a MP. Thus a single episode of VT at 240 beats per minute might be treated with a shock without notification of an ME, but four episodes of the same VT over 15 minutes might warrant notification.

Device 16 may be a microprocessor, a group of microprocessors or other computational devices as is known in the art. When preset criteria for ME notification have been met, it signals a ME by sending notification signal 18 to first transmitting/receiving device. "first T/R" 20, which is transmitted to the ME. 20 may consist of a single unit which performs both transmitting and receiving functions, or separate units. The transmission methods are discussed hereinbelow. Along with the notification signal, the logic device will send medical data 32 for the ME to evaluate. The data may include (a) actual signals 15, (b) a processed form of 15, e.g. filtered, compressed, etc., (c) a further refined form of 15 [e.g. beat to beat measurements of cardiac RR intervals], and (d) still further refined forms of data [e.g. the information that 17 of the last 20 beats were at a rate greater than 200].

The ME has a variety of options upon receipt of this information, discussed hereinbelow. If the ME chooses to treat, a real time remote control signal 22 is received by 20 and sent to 16. The logic device is operative to pass two types of control signals to the medical treatment device which it controls, (a) remote signals 24 which initially originate with the ME, and (b) local signals 28 generated by the logic device, based on its analysis of 15.

The logic device may prioritize among ME control signals 22 and its own control signals in a variety of ways:
  a) It may always give priority to ME control signals over its own internally generated control signals; In such a situation, following notification, only the loss of communication with the MP would result in local control (i.e. control of the
  b) In the presence of ME control signals, it may not even generate its own control signals;
  c) It may always provide therapy unless there is a specific signal 22 which inhibits its providing therapy;
  d) It may provide therapy along with the ME in an "OR" logic fashion, such that either one may cause 16 to cause 26 to treat.

Memory device 17 is linked to the logic device. It may be used for the storage of information about patient events, the storage of programs for medical treatment device management and sensor signal processing, the temporary storage of information during a communication exchange with a ME, the storage of write-once-only information, and the storage of rules for notification management.

Figure 2A:
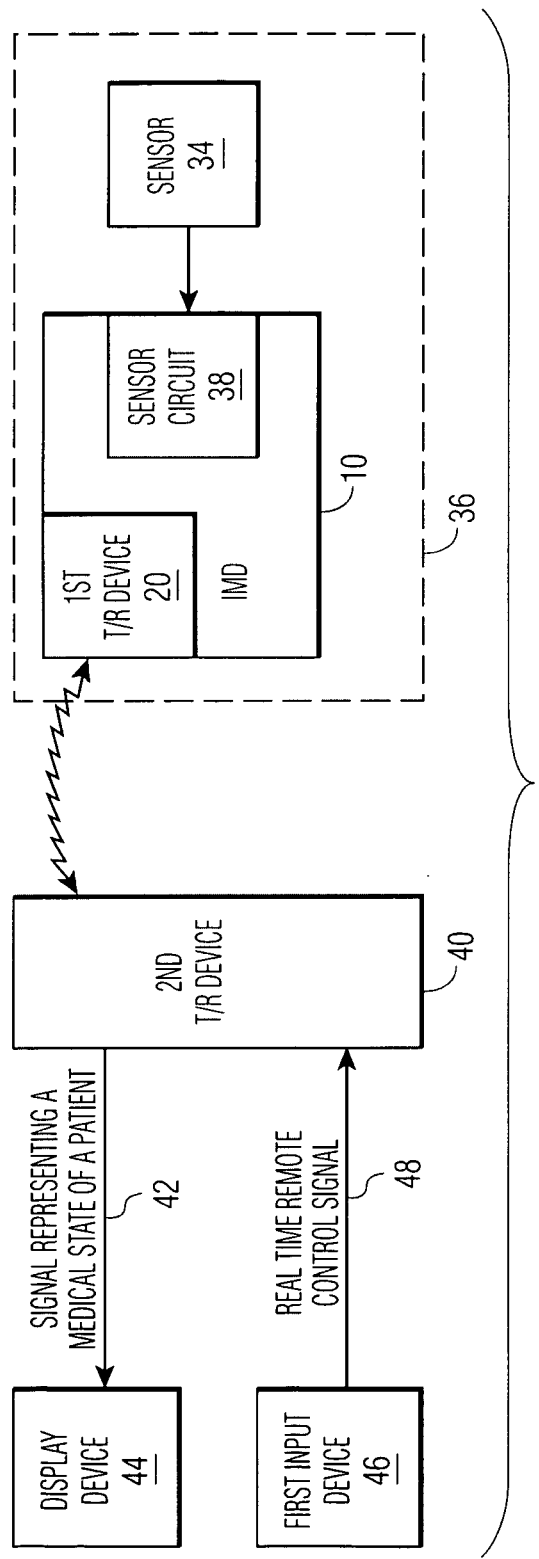
FIG. 2A is a representational block diagram of a system including an IMD, a sensor and a remote station to be operated by a human medical expert.

FIG. 2A shows an embodiment of the invention in which IMD 10 communicates through it first T/R, with a second T/R device 40. 40 provides signals representing a medical state of a patient 42 to be displayed on display device 44. First input device 46 allows an ME to send real time remote control signals to 40, for transmission to 20. 10 and at least one sensor 34 is implanted inside the body of a patient 36. Examples of possible sensors include a pacemaker wire (for sensing cardiac electrograms), a defibrillator lead, a transducer for measuring glucose concentration, a system of conductors for measuring transthoracic impedance, etc. In the embodiment of the invention shown in FIG. 2A, sensor information from 34 is coupled to the sensor circuit 38. IMD 10 transmits the information representing the sensor information (which may be the actual sensor information) via 20 to 40, for display by 44. A human ME may then determine the appropriate treatment, and input it to 46. Signals 48 representing the treatment are transmitted from 40 to 20, thereby to affect the function of 10.

Figure 2B:
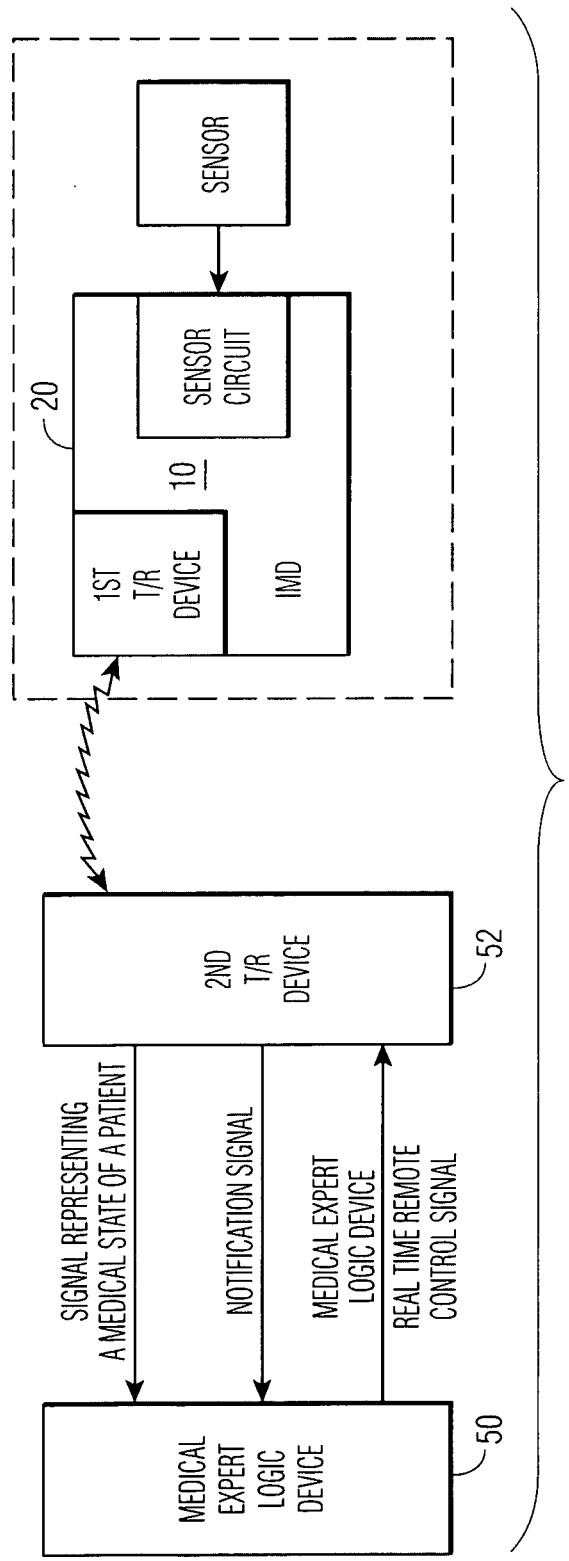
FIG. 2B is a representational block diagram of a system including an IMD, a sensor and a remote station operated by a medical expert computational device.

FIG. 2B shows an embodiment of the invention in which the ME is a medical expert program or group of programs which run on a computational device 50. Each of the signals to and from the first T/R (18, 22 and 32 in FIG. 1) are transmitted between first T/R device 20 and the $2^{nd}$ T/R of shown herein 52. A device such as 50 would have advantages over the logic device of the IMD including: (a) a much larger memory capacity, such that information may be stored concerning (i) other medical data from this patient; (ii) other medical data from other patients with a similar condition, (iii) performance data about IMD 10; (b) ability to update the database for 52 easily and frequently; and (c) ability to update the algorithms run by 50 easily and frequently.

FIG. 2C shows an embodiment of the invention in which IMD 10 in patient 36 communicates with a computer ME 60, which in turn communicates with a human-based ME 70. First communication device 62 in 60 communicates with second communication device 72 in 70; the communication may be either wireless, indicated by signals 66 or wired, indicated by signals 64. The function of 74 is analogous to that of 44 in FIG. 2A, and the function of 76 is analogous to that of 46 in FIG. 2A. The route of the human real time remote control signal is from 76 to 72 to 62 to 63 to 61 to 11 to 10. In an alternate embodiment, the human control signal could be coupled from 62 directly to 61. In yet another embodiment, an RF signal from 72 could be sent directly to 11. The human ME may use each of the following in the process of making a decision: (a) signals (processed and unprocessed) from one or more sensors 35 in patient 36, (b) signals indicating the analysis by the logic device of IMD 10, and (c) signals indicating the analysis by expert logic device 63. There are numerous possible relationships between which determine dominance, in terms of control, among each of (i) the human ME, (ii) device 63, and (iii) the IMD logic device. For example:

a) in one embodiment of the invention, human ME signals, if received by the logic device of IMD 10 take precedence over control signals which may have been generated by the IMD logic device and over control signals generated by the analysis of the medical data by 63;

b) in another embodiment, the human may be overruled if both 63 and the IMD logic device disagree with the human;

c) in another embodiment, an "OR" logic prevails, and any one of the IMD logic device, 63 or the human ME may cause therapy to be delivered;

d) in another embodiment, "AND" logic prevails, and therapy is delivered only if each of the human and 63 and the IMD logic device indicate that treatment is desirable; and e) in another embodiment, any two of the three of the human ME, 63 and the IMD logic device will dominate.

To reliably maintain a system in which the control of an implanted medical device is shared or given over to an outside agent, all possible means to maintain communications integrity must be undertaken. Techniques for improving reliability include but are not limited to: (a) redundant communications, (b) the ability to change a route (e.g. wired vs. wireless [though at some point there must be a wireless segment for the implanted device), (c) the ability to change a communications mode (e.g. different means of signal encoding, as is known in the art), (d) the ability to change power output of an RF or other electromagnetic device, (e) the ability to change the sensitivity of a receiver, and (f) the ability to change frequency or channel or telephone number or internet provider.

Figure 3A:
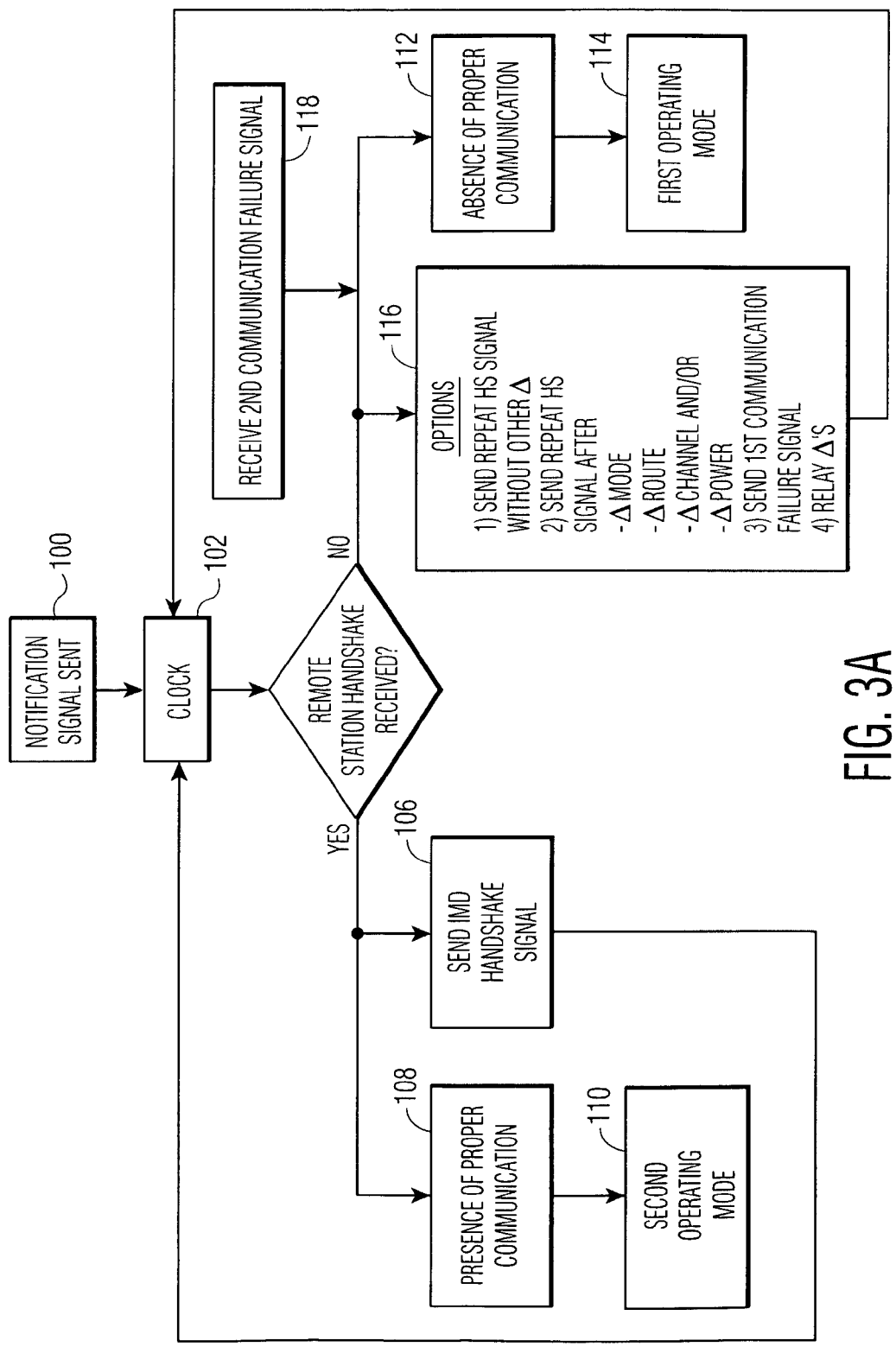
FIG. 3A is a flow diagram of a communication routine for a remotely controllable IMD.
Figure 3B:
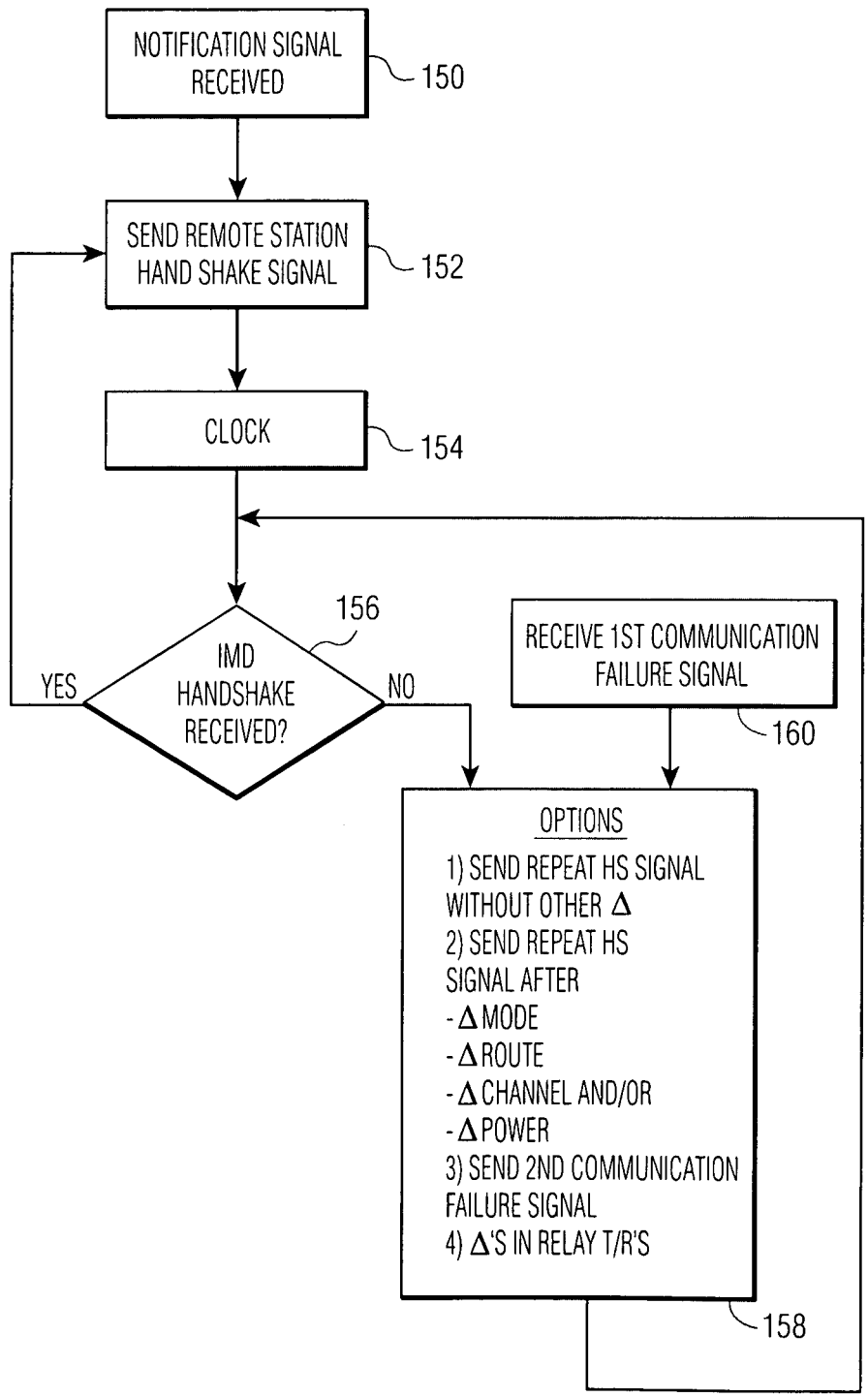
FIG. 3B is a flow diagram of a communication routine for a remote station which communicates with a remotely controllable IMD.

Furthermore, it is important that each of the communicating agents be able to determine whether each segment of the communication path (in each direction) is operative, on a real time basis. For example, if the IMD logic device determines that there has been a break in communication with the ME, it must immediately (a) revert to autonomous operation, and (b) take whatever corrective means it can to restore proper communication. Thus, one embodiment of the invention is operative to cause immediate restoration of device control by the IMD logic device, in the event of a break in communications. To accomplish this, a handshaking routine is operative. FIG. 3A shows the routine at the IMD, and FIG. 3B shows it at the remote station. (Hereinbelow, communication between the IMD and the remote station through one or more relay devices is described. Handshaking routines, known in the art, are possible between (a) each 'adjacent' communicating component in a string of devices, as well as (b) an overall handshake between the remote station and the IMD.

Referring to FIG. 3A, which shows one possible semi-continuous handshaking routine at the IMD, following the transmission of notification signal 100 by the IMD, an interval of time measured by clock 102 is allowed to elapse, waiting for a response, in the form of a remote station handshake signal. If the remote station handshake signal is received in a timely manner, block 104 leads to blocks 106 (resulting in the transmission of an IMD handshake signal by the IMD) and 108, a declaration of the presence of proper communications. The presence of proper communications allows for a second IMD operating mode, in which the IMD is controlled remotely. Block 106 leads to another waiting period determined by 102. In the presence of proper communications, the flow diagram will continuously cycle from 102 to 104 to 106 to 102 . . . . However, if there is an interruption in communications, such that a remote station handshake signal is either not received, or not received in a timely manner, block 104 leads to 112 and the declaration of the absence of proper communications. 112 leads to 114 and a first IMD operating mode. In the first operating mode, the IMD is controlled only by the IMD logic device. In this case, 104 also leads to 116, which lists a menu of options directed at restoring proper communication including: (a) repeat transmission of the remote station handshake signal without any other change; (b) change in either mode, route, power or channel/frequency, (c) change in the sensitivity, selectivity or other receiver characteristics of the IMD receiver (not listed in the figure), (d) change in the characteristics or choice of an upstream communications relay unit (see below), etc. Each of these choices then leads to another handshake attempt, and another waiting for a response.

It may be possible to determine whether a break in communication occurred in the IMD to remote station direction, or in the reverse direction by the sending and receiving "communication failure" signals. Thus if the IMD receives 118 a second communication failure signal, it implies that the remote station to IMD leg is intact, and it is the IMD to remote station leg that has failed. This helps direct remedial action. Among the items in menu 116 is the sending of a first communication failure signal, to allow the remote station to gain some diagnostic information about the source of the handshake interruption.

FIG. 3B shows one possible version of a handshaking routine at the remote station. Although the determination of a break in communication is far more important at the IMD end (i.e. so that the IMD may resume autonomous function immediately), there are remedial actions that can be accomplished at the remote station end, therefore making the detection of a handshake interruption valuable at that end as well. At block 150, the notification signal is received from the IMD, leading to the transmission of a remote station handshake signal at 152. If after a suitable delay measured by clock 154, there is no received IMD handshake, 156 leads to 158, with a menu of remedial options which are analogous to those in block 156. The intact handshake loop in the diagram is 156, 152, 154, 156 . . . . The broken handshake loop is 156, 158, 156, 158 . . . .

Many other approaches possible handshaking protocols and apparatus will be obvious to those skilled in the art.

Finally (see hereinbelow), downloading a treatment plan or routine for a currently happening ME-IMD session, for storage in the IMD memory, may allow for the completion of a ME set of treatment steps which were interrupted by a break in communications.

Many implanted devices have a low battery drain and a longevity measured in years. If the same battery that supplies a minimal amount of energy for device function (e.g. cardiac pacing, where the current drain may be 10-20 microamps or less) must also supply a transmitter, then unless there is judicious power management, there may be substantial shortening of device battery life. Among the options for accomplishing this are:

a) programming notification criteria so that the function is not over-used;

b) the placement of one or more relay units (see below) in proximity to the IMD/patient, so that transmission from the first T/R involves only short distances;

c) methods of powering down the first T/R, partially, during a transmission, if possible;

d) monitoring battery function so that as the battery ages, the criteria for notification may be made more restrictive;

e) letting the ME know the battery status during a transmission, so that the ME, recognizing an aging battery or batteries, may take action to shorten the current transmission and limit future ones, perhaps by either (i) remotely reprogramming notification criteria, or (ii) remotely programming transmitter power consumption;

f) having a dual power supply arrangement, where one power supply powers only the device T/R (or only the device transmitter), and one power supply powers everything else in the device. An alternate embodiment of this approach would be to the transmitter (or T/R) battery or batteries to be rechargeable.

Figure 4B:
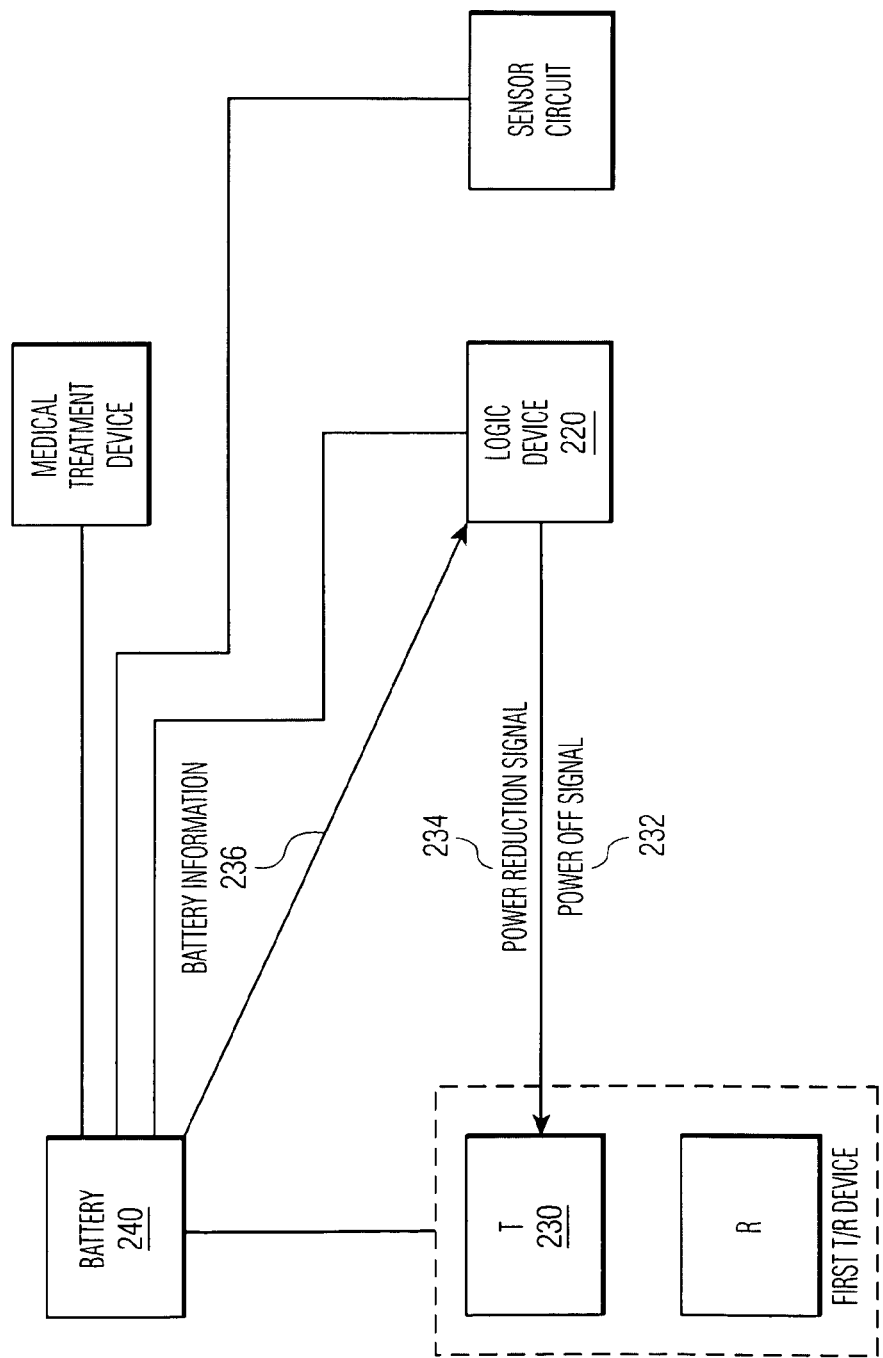
FIG. 4B is a representational block diagram showing locally controlled power management for a remotely controllable IMD with one battery.

Four exemplary ways of handling battery management are illustrated by the embodiments of the invention shown in FIGS. 4A-4D. Hereinbelow, the word battery may refer to a single cell, two or more cells in series, two or more cells in parallel, and may refer to combinations of these. FIG. 4A contains a single battery 200 which supplies each of the components of the IMD. In addition to supplying the components discussed hereinabove in conjunction with FIG. 1, the battery also supplies battery monitoring apparatus 202 with energy. 202 monitors one or more of battery voltage, cell impedance, battery current drain, the droop in cell voltage with increased demand, and indirect measures of battery function (e.g. the charge time of an ICD). The battery information is supplied to the IMD transmitter 206, for transmission to remote station 208, for assessment by the ME. The ME may use the information for management of real-time power consumption (i.e. reduce transmitter power during the current encounter) by sending a signal to receiver 210, which passes the information contained therein to transmitter 206. Alternatively, the MP may reprogram device performance (e.g. notification criteria), by sending a programming command from 208 to 210 to the logic device (which coupling is not shown in FIG. 4A, but is indicated in FIG. 1.

FIG. 4B shows a one battery management approach where management is directed within the IMD, i.e. by the IMD logic device. Information 236 about battery 240 (similar to the information discussed hereinabove in conjunction with FIG. 4A) is processed by logic device 220, and may be used maximize the longevity of the battery, as discussed hereinabove. Besides power reduction signals 234 which reduce transmitter 230 power by a variety of possible values, a signal 232 may be sent to power 230 off. As indicated, 220 may also reprogram itself to accomplish such goals as altered notification criterion.

It is possible to combine the attributes of the power conservation approach shown in each of FIGS. 4A and 4B.

Figure 4C:
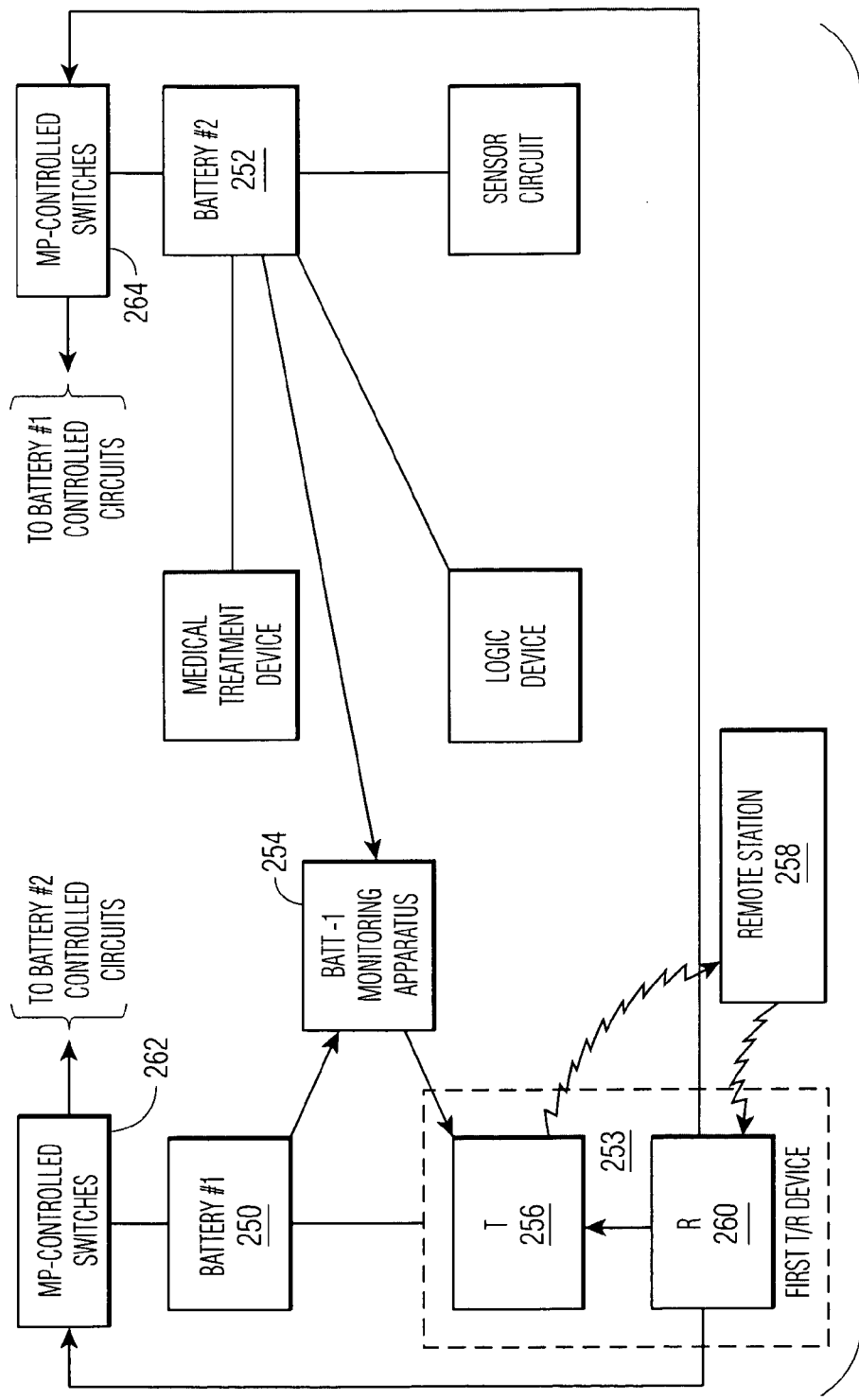
FIG. 4C is a representational block diagram showing remotely controlled power management for a remotely controllable IMD with two batteries.

FIG. 4C shows a dual power supply approach to power management. As shown in the figure, battery 252 powers the device components except for the device T/R 253 (and perhaps the battery monitoring apparatus 254), which are powered by battery 250. Battery information moves from 254 to transmitter 256 to remote station 258 for evaluation by the ME. The ME may control transmitter characteristics by sending a signal from 258 to receiver 260 to transmitter 256. In addition, the presence of a second battery gives the ME some additional options: the use of one of the batteries to perform the function of the other. Thus if battery 252, which controls the IMD in general, is nearing its end of service, and transmitter battery 250 has a substantial remaining energy supply, the ME may cause switching apparatus 262 to divert some or all of 250 energy to perform the functions intended for battery 252 (i.e. non-transmitter function). Similarly, the MP may do the mirror image diversion: In a situation with good 252 energy supply, poor 250 energy supply and the need for an urgent interaction with a ME, switching apparatus 264 may divert energy to transmitter 256 that might otherwise not have been able to be supplied by 250. The ME could learn about the status of battery 252 by information passed along the link from it to 254, and thence to 256 and 258.

Figure 4D:
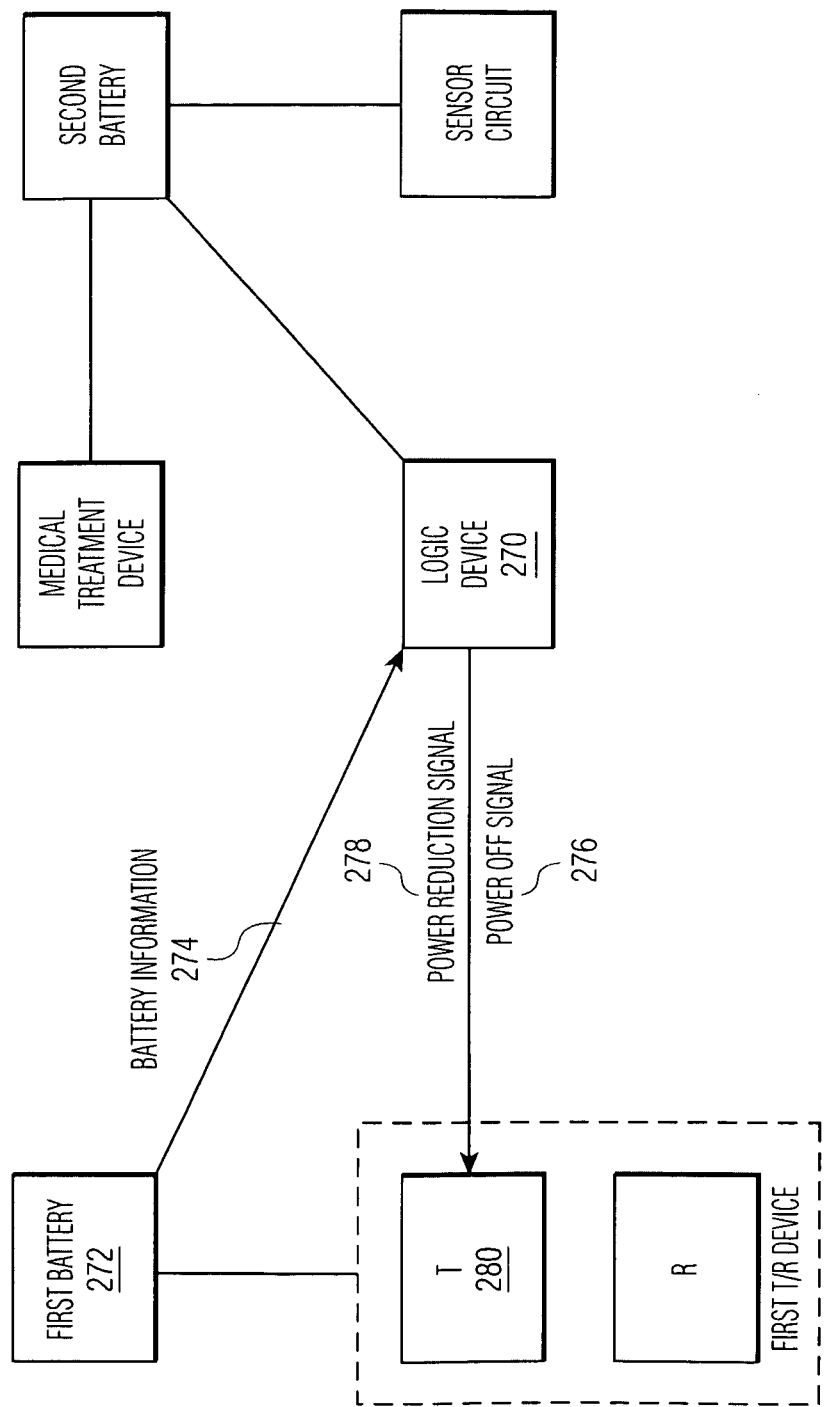
FIG. 4D is a representational block diagram showing locally controlled power management for a remotely controllable IMD with two batteries.

FIG. 4D shows a 2 battery configuration, with energy management by the IMD logic device. All of the functions performed by the apparatus in FIG. 4C could be performed by that in FIG. 4D, except that the source of management commands is logic device 270. 270 processes information 274 about the status and projected longevity of 272, and may use it to either (i) make one or more reductions 278 in the power consumption of 280, or (ii) turn off 276 the transmitter.

Figure 5A:
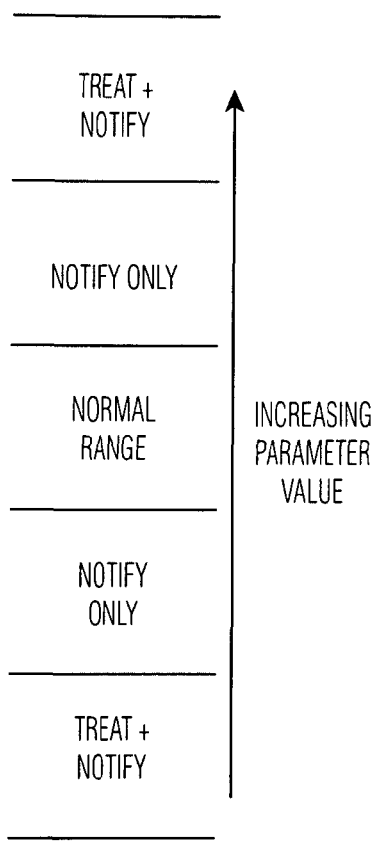
FIG. 5 shows a graphic representation of some possible arithmetic relationships illustrating the notification definition and the parameter abnormality definition.
Figure 5B:
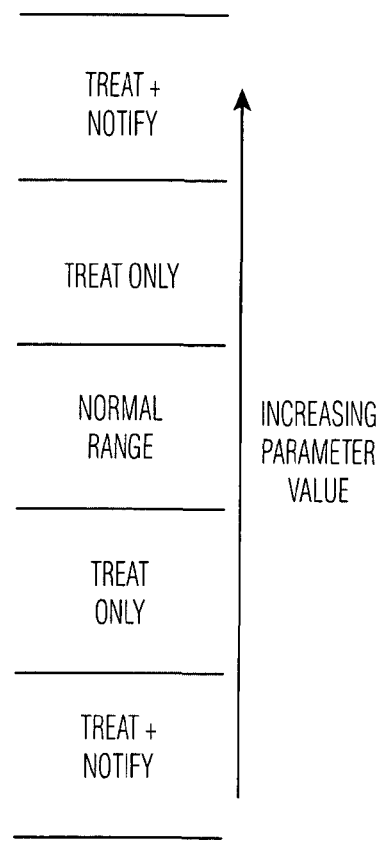

A wide variety of possible triggers for ME notification are possible. FIGS. 5A and 5B illustrate a situation in which a single parameter (e.g. heart rate) is monitored to determine device action. Conventional ICDs (which include pacemaker function) are programmed to treat tachycardias which are above a certain heart rate, and bradyarrhythmias whose rate is below a certain heart rate. The scenario illustrated by FIG. 5A shows a scenario in which a range of rates which is intermediate between the high rate, at which treatment is definitely required, and the normal rate, may be defined as the notification range of rates. For example, an ICD might be programmed to:

a) notify for rates from 140 to 160 bpm and to treat and notify for rates above 160 bpm. The ME, upon notification, would decide whether treatment is required for a rate of say, 150 bpm, and if so, cause the ICD to provide such treatment. The ME might decide (a) to try some gentle treatment such as a non-aggressive anti-tachycardia pacing for the situation, (b) to go ahead and provide aggressive treatment, or (c) to not treat at all. In the latter case, the ME might decide to check the patient at some later time, e.g. by leaving an instruction in the ICD for the ICD to check in with the ME in 30 minutes. The ME might further program altered "second notification" criteria, i.e. if the rhythm normalizes, then over the next 24 hours, the threshold for notification is lower (e.g. 130 bpm).

b) notify for rates from 140 to 160 bpm and to treat (and not notify) for rates above 160 bpm. [This is not shown in the figure.] This saves battery in cases where there is little or no uncertainty about which therapy is the appropriate one.

In the figure, a similar format is programmed for bradyarrhythmia. For example, the pacing circuits may treat when the rate declines to 40 bpm, but may be programmed to notify for rates in the range of 40 to 50 bpm. Alternatively, the programming person might choose not to notify for pacing at 40 bpm (i.e. treat without notification).

FIG. 5B shows a format in which the ME is notified (and treatment is given) for values of a parameter that are extreme but not for values that are only moderately abnormal. For example, the ME might be notified for tachycardia that was treated whose rate was 260 bpm, but not for tachycardia which were treated with rate less than 200 bpm.

The aforementioned scenarios reflected by FIGS. 5A and 5B concern rather simply notification criteria. More complex ones may depend on the results of multiple different parameters from multiple sensors, and their evolution over time. Still more complex scenarios may depend not just on the measured values of these parameters, but complex mathematical functions of them.

Figure 6A:
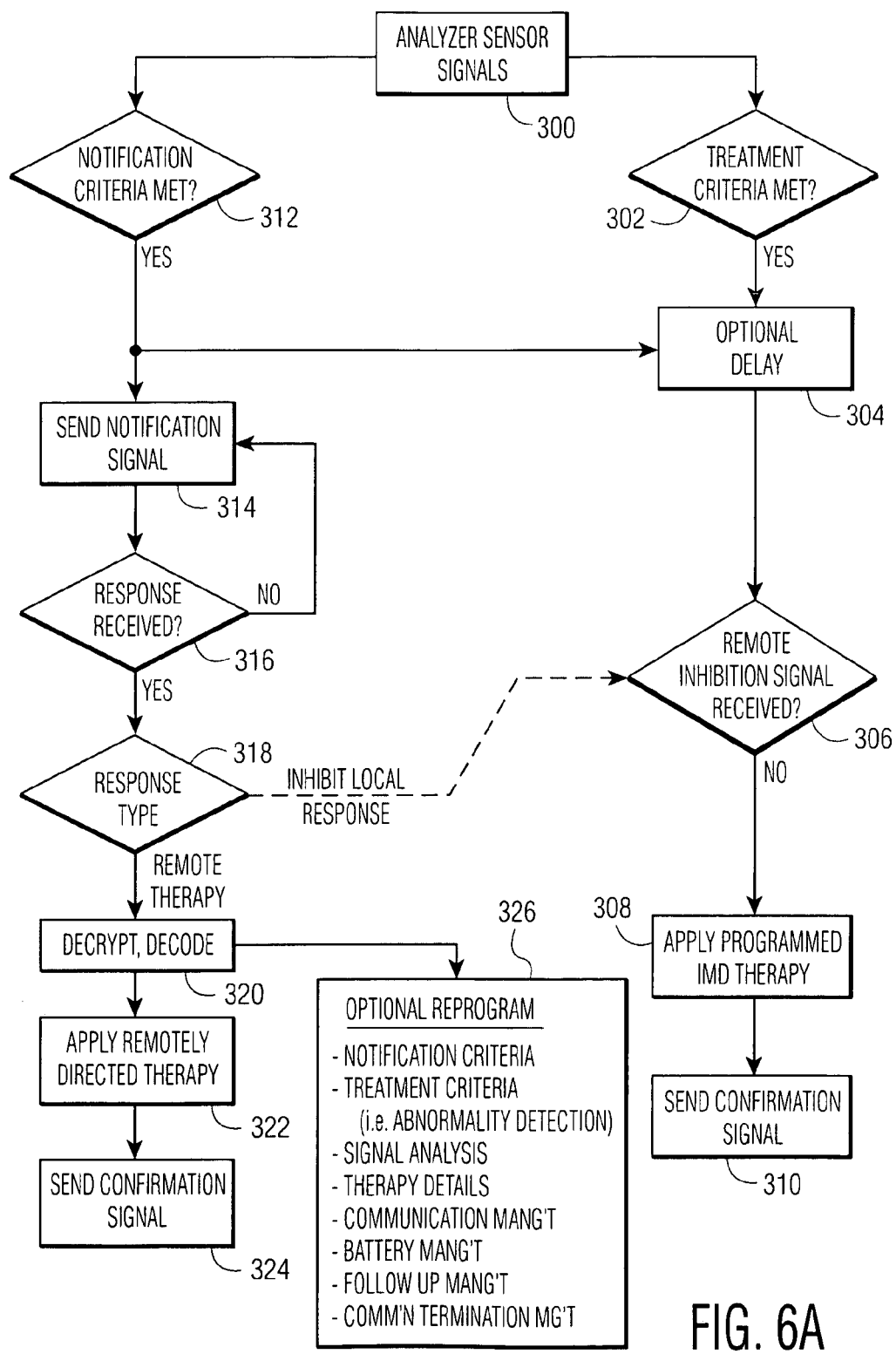
FIG. 6A shows a flow diagram of one possible algorithm for notification.

Once notification has occurred, the other dimension of interaction between the IMD and the ME, is how much control the ME has access to, following notification. FIG. 6A shows a scenario in which the ME is given essentially complete control. The right hand side of the figure shows the essential features of operation when the device operates autonomously. Following detection of a parameter value 302 which requires therapy, the device applies the pre-programmed therapy 308, and optionally transmits a confirmation signal, block 310, indicating that therapy has been provided. However, if notification criteria have been met, 312, the IMD sends a notification signal, 314, for receipt by a remote station, and awaits a response, 316. Once the ME is in communication with the IMD, the ME may both positively and negatively control the device; That is, the MEP may choose to inhibit (block 318 to 306) an action that the device, if operating autonomously, would have performed. Alternatively the ME may choose to cause the device to deliver therapy, even though the IMD program may not have called for this. In such a circumstance, block 318 leads to 320, in which an ME command is decrypted and decoded, and then to 322, in which the therapy instructions are carried out, followed by the sending of confirmation signal 324.

Since the establishment of a communication link between the ME and the IMD may take a short time, an optional delay 304 is added in before the IMD acts autonomously, in a situation when notification has occurred. This is indicated by block 312 inducing optional delay 304, to prevent autonomous IMD therapy before the ME can be involved.

The ME has a number of options for influencing the management of future events post notification, shown in block 326. In a preferred embodiment of the invention, the ME may reprogram (a) notification criteria, (b) the definition of what constitutes and abnormality, in terms of autonomous device functioning, (c) aspects of sensor signal analysis, (d) the details of therapy during autonomous device functioning, (e) communication management [route, mode, channel, etc.], (f) battery management, (f) followup management (the ability of the ME to ask for a callback from the IMD) after a ME-managed-event, to report patient status), and (g) communication termination management (e.g. how long until communication ends after [i] a successfully managed event, and [ii] an event in which communication failed during the event).

Figure 6B:
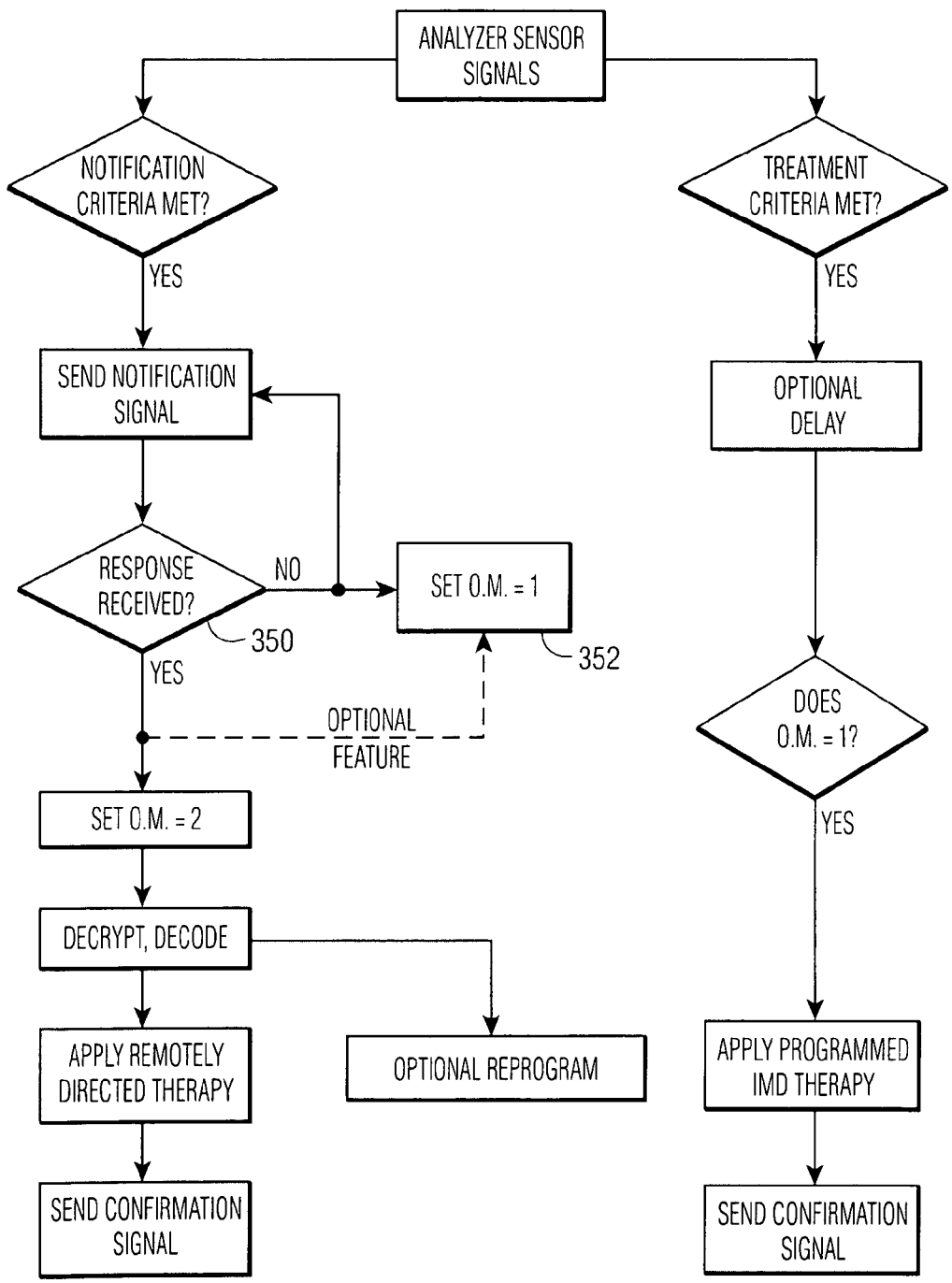
FIG. 6B shows another flow diagram of one possible algorithm for notification.

FIG. 6B shows another management scenario. Two operating modes are defined for the IMD. In a first operating mode (O.M.=1, in the figure) the IMD logic device is in control of therapy, while in a second operating mode (O.M.=2, in the figure), the ME is in control. The scenario shown in 6A involved moment to moment choices by the ME of whether to inhibit an IMD function; In the scenario in 6B, all IMD function is inhibited in the second operating mode, unless (a) the ME chooses to return the control to the IMD (block 350 to 352 via broken line indicating optional feature), or (b) communication fails [350 to 352 via solid arrow]. In other aspects not explicitly mentioned, the algorithm in FIG. 6B is identical to that of 6A.

Figure 6C:
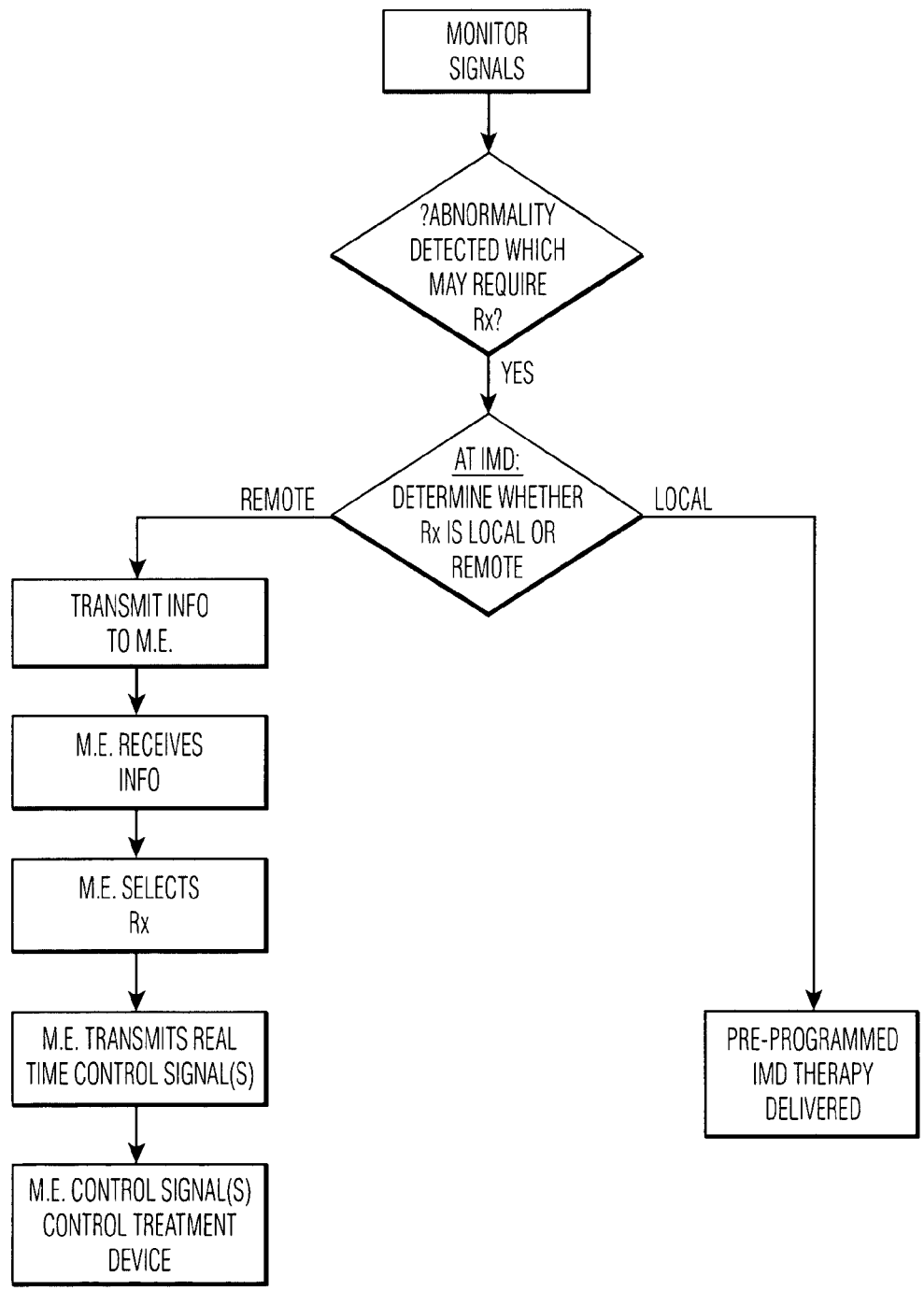
FIG. 6C shows another flow diagram of one possible algorithm for notification.

FIG. 6C shows a different algorithm. In this case, the decision between remote and local management is made (a) early on [i.e. before the ME is involved], and is made by the logic device of the IMD. Other aspects of the figure not specifically discussed are similar to those in already discussed figures.

Figure 6D:
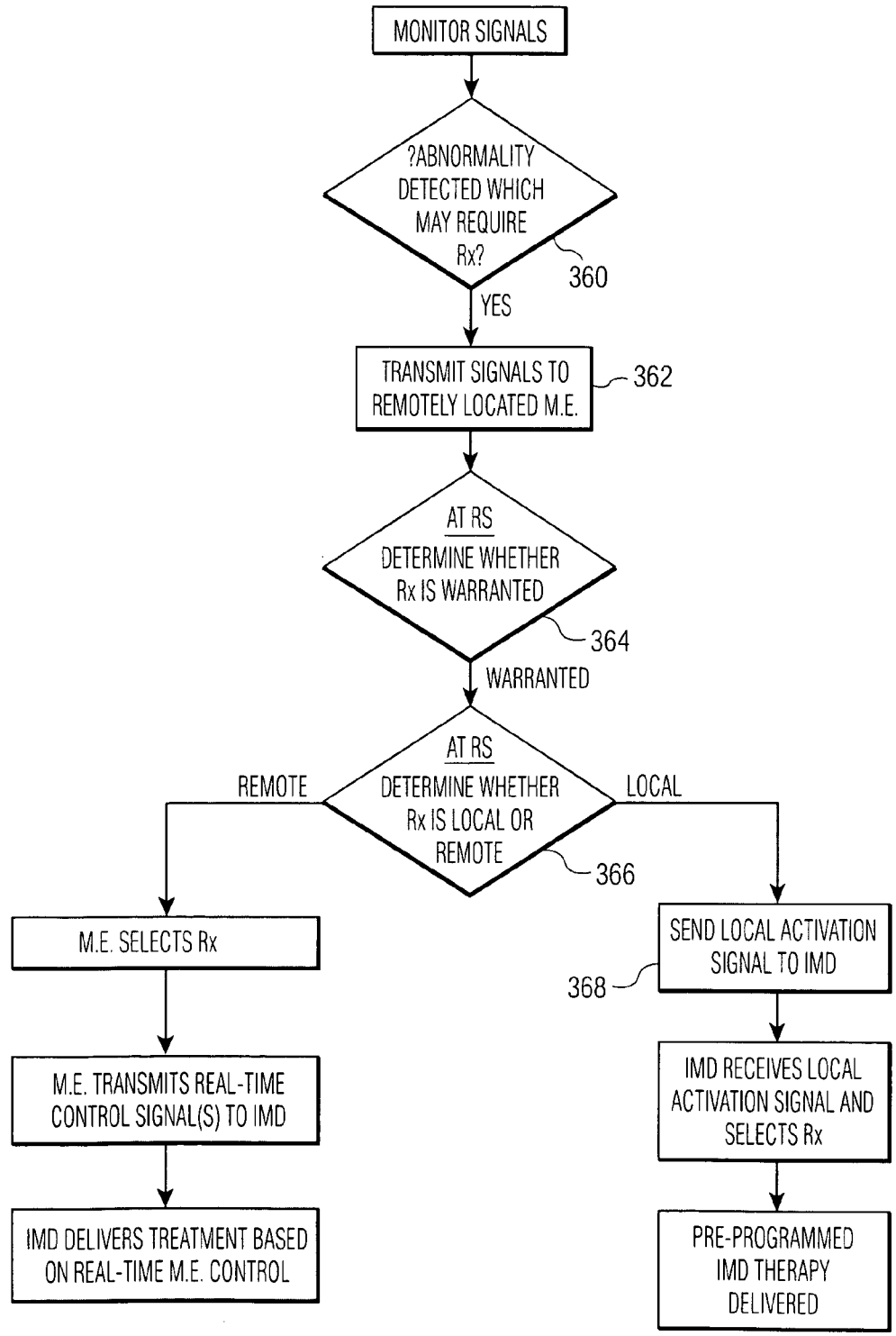
FIG. 6D shows another flow diagram of one possible algorithm for notification.

FIG. 6D shows another algorithm in which the remote station (RS) is given a particularly high level of priority. If an abnormality is detected by the IMD which may require treatment 360, signals are transmitted to the ME 362, at which point, two determinations are made: (a) Is therapy warranted [block 364]? and (b) Is the source of therapy-related choices to be local (i.e. the IMD) or remote (i.e. the ME)[block 366]? If the source of therapy is to be local, the ME returns control to the IMD. Other aspects of the figure not specifically discussed are similar to those in already discussed figures.

Other scenarios in which the ME does not have top priority have been discussed hereinabove.

Figure 7:
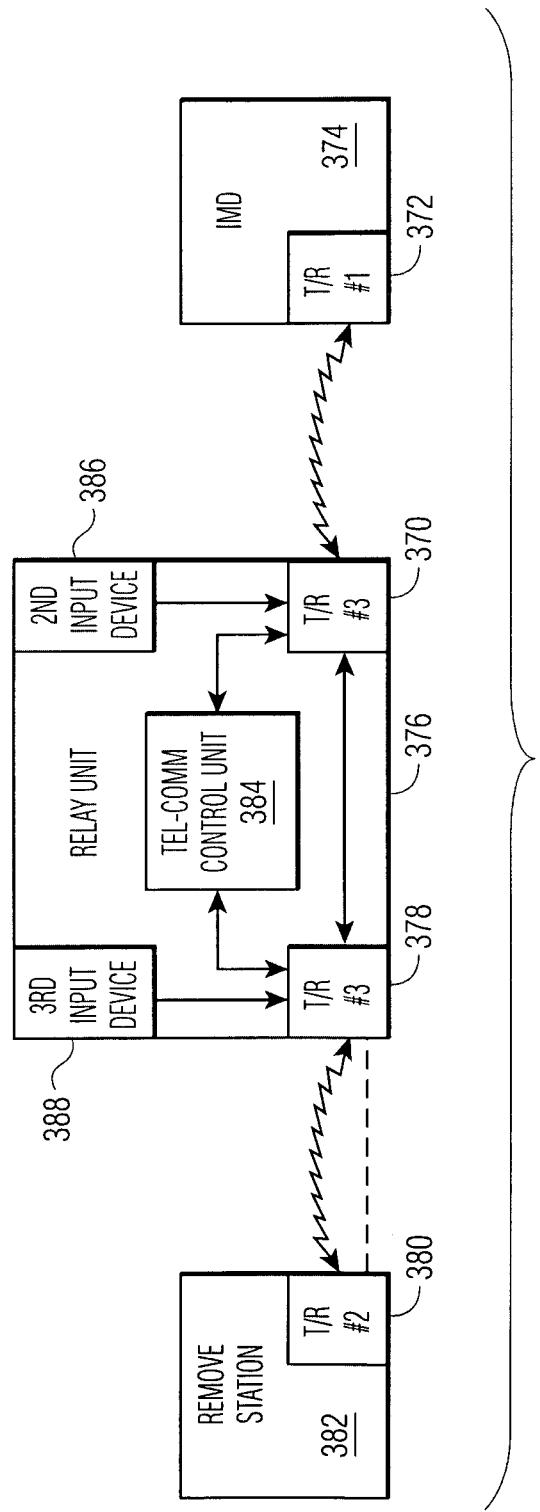
FIG. 7 shows a representational block diagram of a communications relay and its links to an IMD and a remote station FIG. 8 show an overview of one approach to ICD management.

Since battery conservation is a major concern with IMDs, and since wireless communication is a feature, the most efficient way to manage such devices is to provide one or more relay units between the IMD and the ME. Having one such unit in close proximity to the IMD will help to limit IMD battery depletion. Many possible relay units may be designed, and are known in the art. The essential features of such a unit are shown in FIG. 7. A fourth transmitting and receiving device, "fourth T/R" 370 communicates wirelessly with the first T/R 372 of the IMD 374. 370 is linked within relay unit 376 to a third T/R 378. The communication of the third T/R with the remote station 382 is via the second T/R 380. The communication between 378 and 380 may be wired (broken line) or wireless. It may involve no intervening communication device, or a number of such devices. It may involve a public telephone carrier or a private network, and may involve the Internet.

376 contains telecommunications control unit 384, which may adjust the operating characteristics of the third T/R to optimize communication with the remote station, and adjust the operating characteristics of the fourth T/R to optimize communication with the IMD. An optional second input device 386 could allow a local person or the patient to have some or complete control of the IMD; An optional third input device 388 could allow a local person or the patient to send a signal (e.g. a notification signal) to the ME. This could be used in a case where the patient feels that observation and potential ME intervention is warranted.

The following description details a preferred embodiment of the invention, entailing an ICD as the IMD. "MP" refers to a medical professional, which is the human version of the aforementioned ME.

Hereinabove and hereinbelow, ICD is intended to include:
  A) devices which can administer a defibrillation shock; and
  B) devices which can administer a defibrillation shock and can administer cardiac pacing. It is to be understood that this technology may be used in any implantable medical device, and any remotely controlled critical system.

Features of the Invention

1) The Implantable Cardioverter Defibrillator ("ICD") may initiate the communication between itself and the Central Station ("CS.") Mechanisms for this are illustrated.
2) The "control unit" referred to in Ser. No. 10/460,458 may be:
  A) a cellular telephone or other personal communication devices (such as a Blackberry®) as are known in the art.
  B) the Stationary Unit referred to in Ser. No. 10/460,458; and
  C) any relay unit whose purpose is to amplify the signal as it is passed along between ICD to CS.
  Hereinbelow, the unit which serves as the communications hardware link between the CS and the ICD shall be referred to as the repeater unit ("RU").
3) Means within the ICD may select alternate mode of communication (e.g. a public or private telephone network, or the internet) and may select alternate routes of communication (e.g. in a multi-segment communication, selecting each segment of the total communications link.
4) Handshake signals may be exchanged between:
  A) the CS and the RU;
  B) the RU and the ICD; and
  C) the CS and the ICD.
The handshake signals may be used to indicate the presence or absence of communication signals between two components (e.g. the ICD and the RU) or to indicate the quality of the signals.
5) If the handshake signals indicate either an absent communications link or a poor quality one, the handshake signals may be used to cause the ICD to:
  A) select an alternate mode of communications;
  B) select an alternate route of communications;
  C) increase the power output of the ICD transmitter;
  D) increase the sensitivity of the ICD receiver.
6) The communications route from the ICD to the CS may involve multiple segments. These segments may include:
  A) an ICD to RU segment;
  B) one or more RU to RU segments;
  C) a RU to CS segment; and/or
  D) a direct ICD to CS segment.

7) Ser. No. 10/460,458 presents two formats for ICD control by a remotely located medical professional ("MP"):
  Format A) In one (claim 219 and the 24 dependent claims which follow), the MP has primary control, and, in the absence of proper communication between the ICD and the MP, the ICD is in control;
  Format B) In the other (claim 244 and the 25 dependent claims which follow), the ICD has primary control. The MP may overrule the ICD on a therapy decision, if he deems this to be desirable.
  Feature 7 presents an approach in which the choice between Format A and Format B may be:
    A) "hardwired" into the ICD;
    B) irreversibly programmable (using a PROM, EPROM, EEPROM, etc., as is known in the art)
    C) programmable by the medical professional who is responsible for programming the patient's ICD an a routine basis;
    D) programmable by the MP, at the time of a medical emergency which has caused the ICD to communicate with the MP; and/or
    E) programmable by the ICD, at the time of a medical emergency which has caused the ICD to communicate with the MP.
8) When the ICD initiates a communication with the CS, there may be a 2-or-more tier format such that:
  A) 2 or more levels of emergency are defined;
  B) for each level, a greater degree of "communications aggressiveness" (on the part of the ICD) is defined.
For example:
  2 levels of emergency:
    Moderate emergencies include ventricular tachycardia ("VT") at rates less than 160;
    Major emergencies include a) VTs at rates greater than or equal to 160 and b) VTs or ventricular fibrillation ("VF") requiring a shock.
  The corresponding two levels of communication aggressiveness would be:
    For Moderate emergencies: a) no ICD transmitter output power boost (see below); and b) a small number of repeat attempts by the ICD to contact the CS; and
    For Major Emergencies: a) one or more ICD transmitter output power boosts; and b) a large number of repeat attempts by the ICD to contact the CS.
Examples with 3 or more levels are obvious.
There is also the possibility of moderate emergencies (or the lowest level of emergency in a three or more level setup) resulting in no attempt at communication by the ICD.
9) Referring to 8) above, the definition of each level of emergency may be:
  A) "hardwired" into the ICD;
  B) irreversibly programmable (using a PROM, EPROM, EEPROM, etc., as is known in the art)
  C) programmable by the medical professional who is responsible for programming the patient's ICD an a routine basis;
  D) programmable by the MP (after communication between the MP and the ICD has been established), at the time of a medical emergency which has caused the ICD to communicate with the MP; and/or
  E) programmable by the ICD (after the event which calls for a communication between MP and ICD); and/or
  F) programmable by the ICD (during the event which calls for a communication between MP and ICD), if ICD circuitry determines that battery conservation requirements dictate a shut-down of the communication link.

10) Options based on battery reserve of ICD:

If hardware/software within the ICD determines that the ICD battery reserve is low, ICD options include:

A) terminate the communication;

B) send a message to the MP indicating the low reserve, and then terminate the communication;

C) lower power output and attempt to continue the communication; (This step may be repeated one or more times.); and/or D) continue the communication with output as is, and repeat assessment at a future time.

11) End of communication options:

The communication may end:

A) because of low ICD battery reserve, see Feature 10), above;

B) because the MP determines that further communication is not warranted; and/or C) because the ICD logic unit determines that further communication is not warranted.

12) Identification-related issues:

Privacy in the communication between the ICD and the MP to be maintained:

A) Encryption and decryption per means and methods:

i) in Ser. No. 10/460,458; and ii) others, known in the art;

B) An identification system wherein any ICD requires proof of MP identification, before and during and communication session.

13) The download of contingency plans from MP to the ICD, as soon as possible after the exchange of information begins. The purpose of the contingency plan download is to have a management strategy in place within the ICD, should the ICD-MP communication get interrupted midway through the event. Although the basic system calls for the ICD to revert to its programmed behavior in the event of communications interruption, the MP may desire to leave a temporary plan in place, to be used for the remainder of the current medical event. The MP may update the contingency plan as needed, as the medical event progresses.

An example of such a contingency plan would be more aggressive (or less aggressive anti-tachycardia pacing, prior to defibrillator shock). Another example would be to eliminate all intermediate energy shocks, and deliver only high energy shocks. Numerous other examples will be apparent to those skilled in the art.

Figure 8:
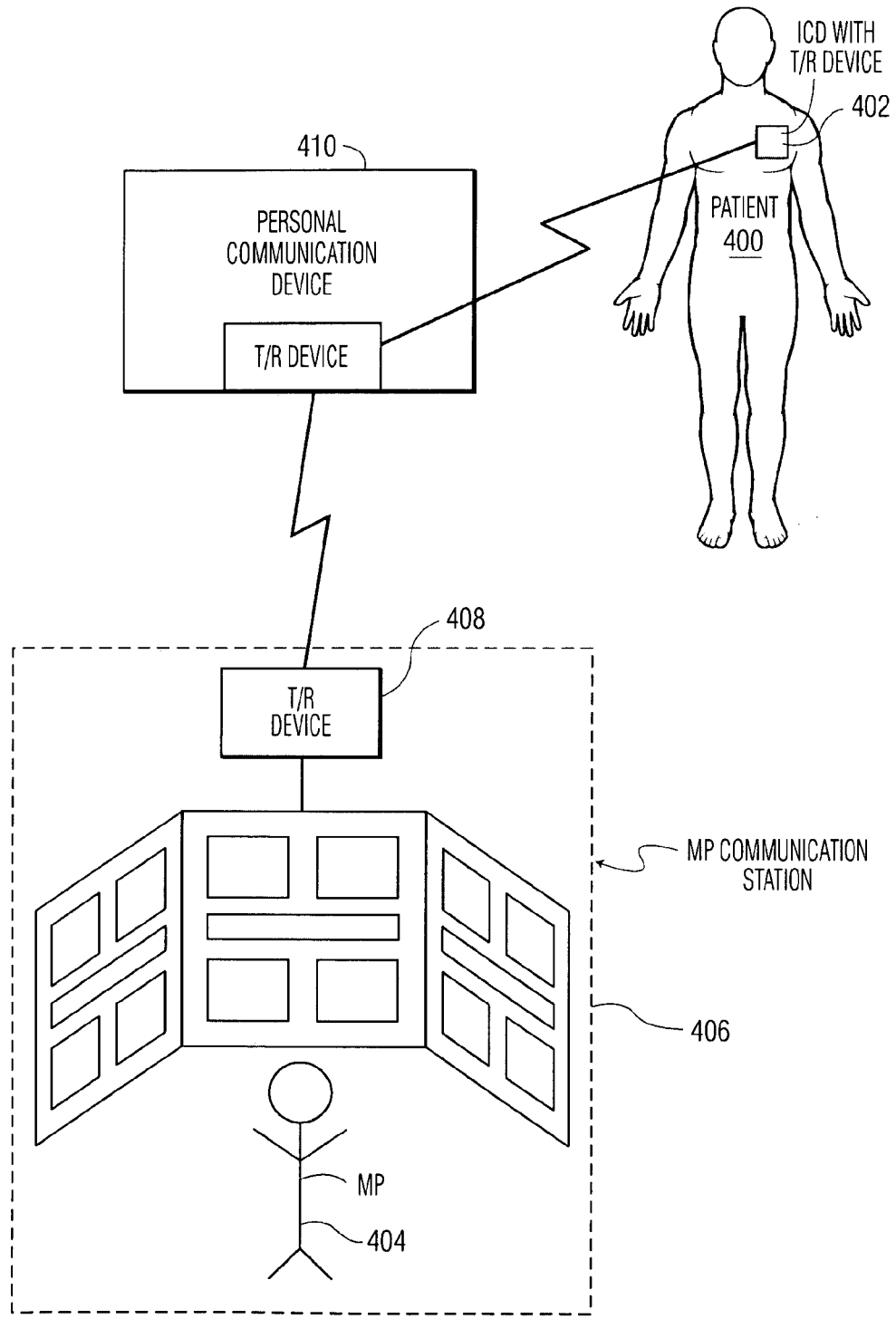

Referring to the figures, which show additional documentation of the means and methods of accomplishing the above 13 features:

FIG. 8 shows a patient 400 with and ICD 402 which communicates with a MP 404 at a MP communication station 406. 406 may be a central station as described in Ser. No. 10/460,458 or a central or peripheral station as described in Ser. No. 11/502,484. The ICD antenna is not shown, but in FIGS. 8-10, it is to be understood that the ICD has one or more antenna which allows it to properly communicate.

The communication route is in either direction between:

A) the T/R device within the ICD;

B) the T/R device within personal communication device 410; and

C) the T/R device within the MP communication station.

The communication route may also be directly between the T/R device within the MP communication station and the T/R device within the ICD.

Figure 9:
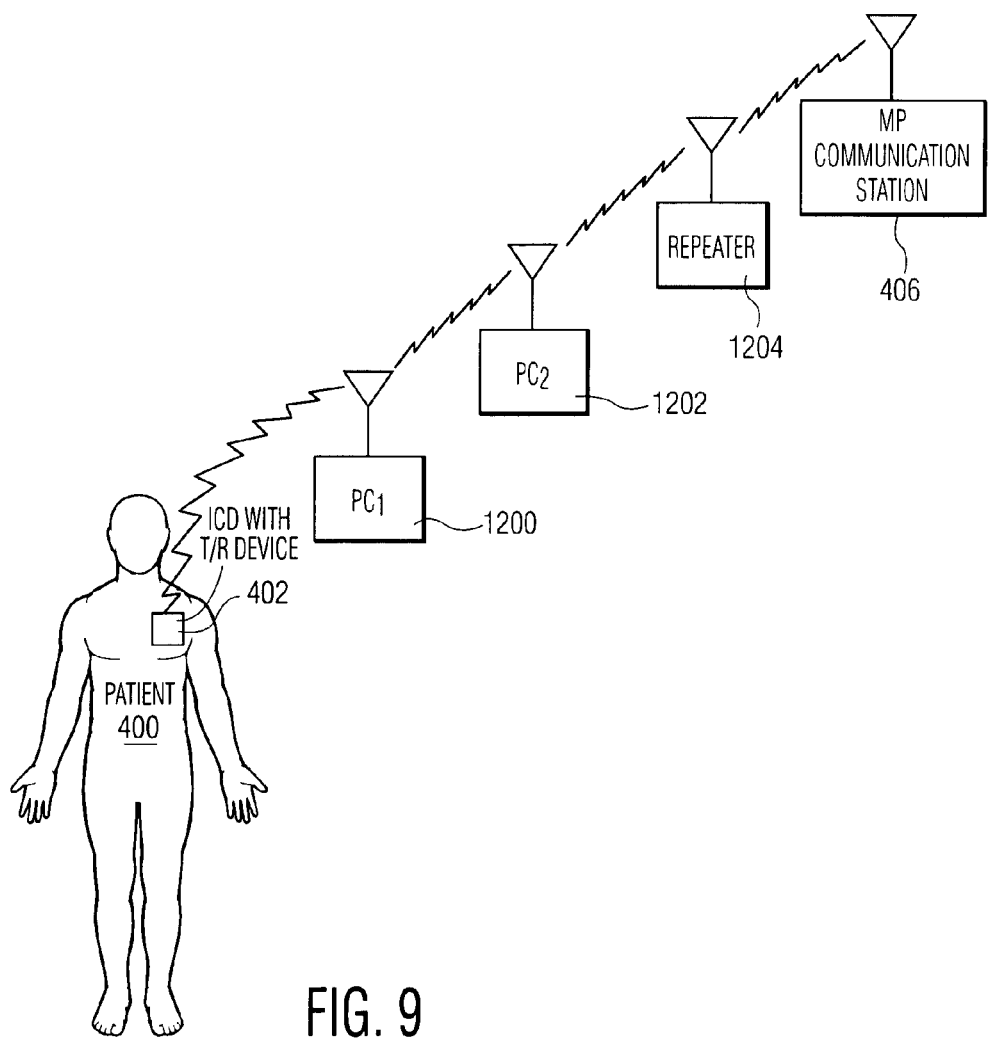
FIG. 9 shows a representational diagram of communication with multiple relays.

Referring to FIG. 9: It is also possible to have two or more intermediate communication links between the ICD T/R and the T/R of the MP communication station. In FIG. 9, there are two personal communication devices 1200 and 1202 and a repeater unit 1204 (as discussed above). Possible arrangements include:

A) two or more personal communication devices and no repeater units;

B) one or more repeater units and no personal communication devices; and

C) one or more repeater units and one or more personal communication devices.

It is also possible that the communications route would change during a single medical event. This could occur if either the MP or the hardware/software within the ICD determines that a change of route is desirable.

The antennae shown for 406 may, at times, not be used, since at times, communication with 406 may be via "land line."

Figure 10:
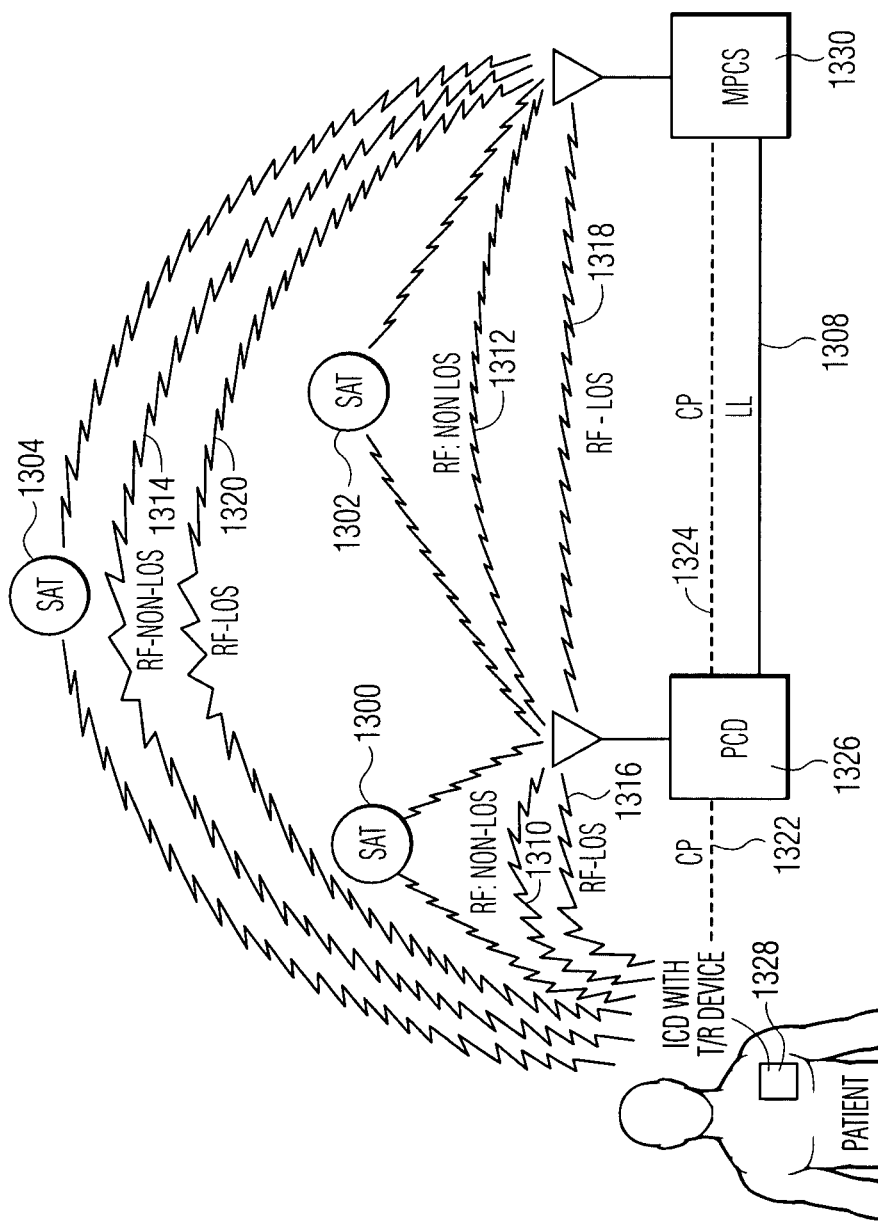
FIG. 10 shows a representational diagram of ICD communication via a personal communication device.

FIG. 10 shows that each segment of the communication route may be:

A) via satellite(s) (1300, 1302 and 1304 in the figure, each of which may represent a single satellite or an array of multiple ones);

B) via a non-line-of-sight radiofrequency link (1310, 1312, 1314);

C) via a line-of-sight radiofrequency link (1316, 1318, 1320);

D) via a public or private telephone network;

E) via cell-phone and/or personal communication device network (1322, 1324);

F) in the links beyond the ICD link, via "land lines 1308;" and/or

G) combinations of A-F

The PCD 1326 in figure PCD in FIG. 10 may be replaced by a wireless router such that the communication between the ICD and the MP is ICD 1328←→wireless router←→internet ←→MP communication station 1330. The route from the wireless router to the communication station can have a wide variety of configurations, as is known to those skilled in the art.

Figure 11:
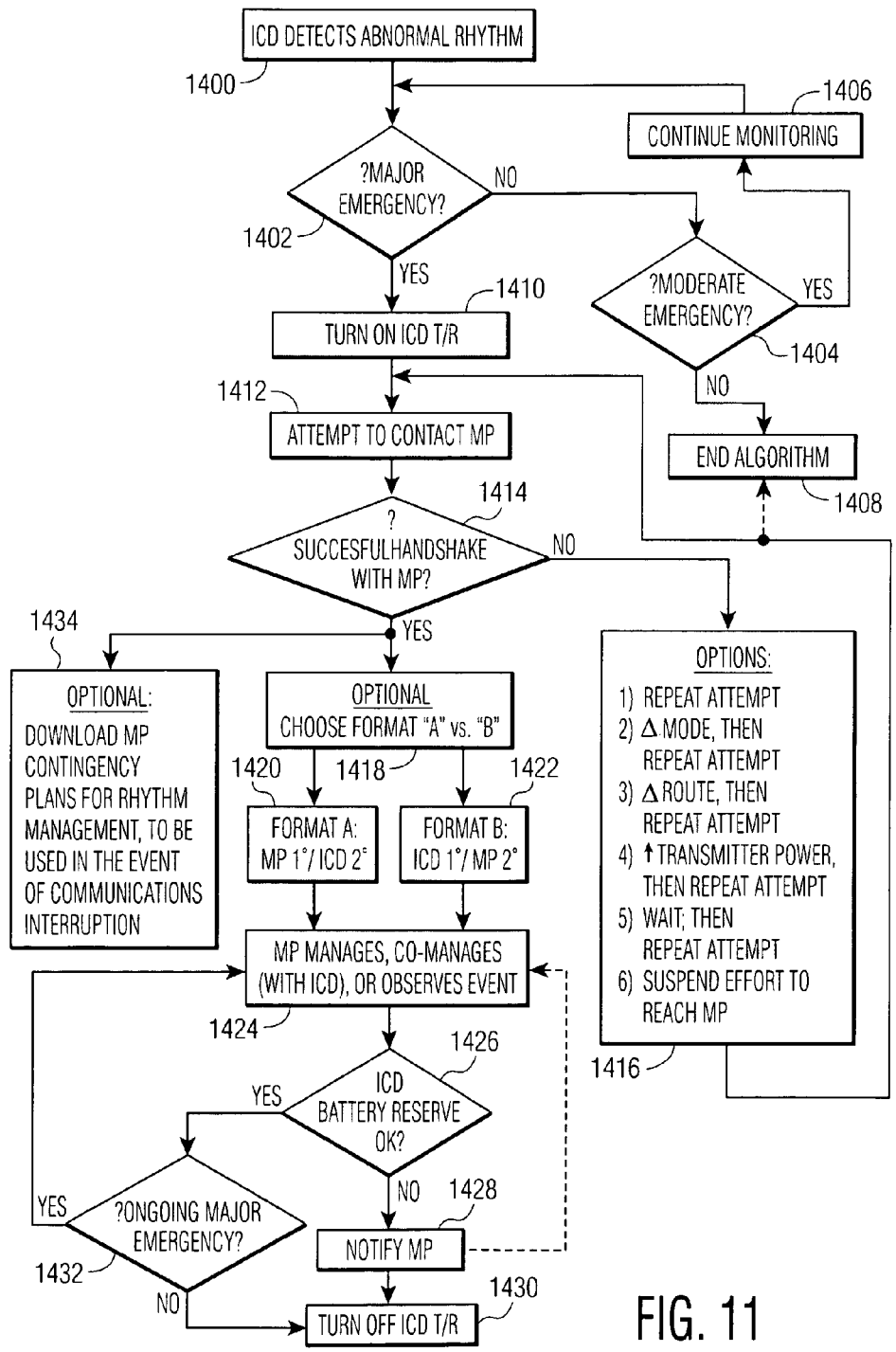
FIG. 11 shows a flow diagram of an ICD management algorithm allowing remote notification and management.

FIG. 11 shows one possible algorithm for allowing the ICD to communicate with a MP communication station, with or without an intervening repeater unit/cell phone/stationary unit/control unit.

If/when the ICD detects an abnormal heart rhythm that requires action, may require action or requires analysis, block 1400, it determines whether the rhythm requires communication with the MP. One method of determination is to classify rhythm abnormalities as either major or not major, and to communicate if the rhythm abnormality is major. This determination is made at block 1402.

The figure shows a setup with two levels of emergency, as described in Feature 8, hereinabove. If the rhythm is determined, block 1402, not to be a major emergency, but is a moderate emergency, block 1404, then continued monitoring, bock 1406, is in order, to monitor for the possibility of the event turning into a major emergency; If this occurs, return to block 1402, and proceed with major emergency section of the algorithm. If there is neither a major nor a moderate emergency, block (either because the emergency condition has resolved, or because there is an abnormality which is less urgent than even the moderate category), the algorithm shown in FIG. 11 ends. ICD monitoring, of course, continues as always.

If a major emergency is detected, block 1410, the ICD T/R is turned on. Not leaving it on continuously saves the battery charge. The ICD then attempts to contact the MP, block 1412. A handshake protocol, which may have some or all elements of that described in Ser. No. 10/460,458 or may have one or more features of other handshaking protocols as are known in the art, ensues, block 1414.

If the handshake is unsuccessful, or (optionally) if the quality of the handshake is sub-optimal, block 1416 lists six possible options. These include:

1) repeat attempt at handshake, using the same communication parameters;
2) change communication mode (as defined in Ser. No. 10/460,458) and repeat handshake attempt;
3) change communication route (as defined in Ser. No. 10/460,458) and repeat handshake attempt;
4) increase ICD transmitter power and repeat handshake attempt;
5) wait, and then repeat the handshake attempt, either with the same transmitter/mode/route parameters or one of more altered ones; and/or
6) suspend efforts to contact the MP.

In the case of the options 1-5, block 1416 leads to block 1412: a repeat attempt to contact the MP.

In the case of option 6, block 1416 leads to 1408 and the algorithm ends. Option 6 may be selected after a pre-programmed number of attempts to reach the MP has occurred. Alternatively, the number of attempts may not be pre-programmed and may depend on the ICD battery status (see hereinbelow), or the level of the emergency.

If the handshake is successful, than the MP will have the opportunity to participate in the management of the emergency. The format for such participation is:

a) pre-programmed Format A (MP control is primary; ICD control is in the event of communications interruption);
b) pre-programmed Format B (ICD control is primary; MP control in the event that the MP chooses to override the ICD decision);
c) either Format A or Format B, with the choice made by the MP at the time of the event; or
d) either Format A or Format B, with the choice made by the ICD based on the severity of the event.

As indicated hereinabove, the aforementioned Format selection is made, block 1418, leading to either Format A/block 1420, or Format B/block 1422. Thereafter the MP either manages, co-manages (with the ICD) or observes the emergency event, block 1424.

The communication between the ICD and the MP may terminate in one of three ways:
A) by necessity, because the ICD battery has reached a point in its discharge, where it is deemed unwise to continue communications;
B) due to the heart rhythm-related emergency having been resolved; or
C) due to an unintended interruption of communications.

In the event of A), block 1424 leads to 1426, which leads to a MP notification, block 1428. This may be followed by:
1) The ICD immediately turning off its T/R, block 1430;
2) The MP deciding to immediately turn off the ICD T/R, block 1430, or,
3) block 1424, the MP deciding to take some additional time to communicate, despite the low battery warning.

Algorithms which omit the warning to the MP of impending ICD T/R shutoff are possible.

In the event of B), block 1424 leads to 1426, which leads to 1432, which leads to 1430.

In the event of C), attempts to re-establish communication occur, as described in Ser. No. 10/460,458. During the time when communication has not been established, the ICD logic unit manages the case.

To avoid a situation where the ICD logic unit must takeover in the middle of an event which the MP was managing in a different manner than would have been executed by the logic unit, the MP may, from time to time download contingency plans to the ICD, block 1434, such that, in the event of an interruption, the ICD has enough of the current MP decision making algorithm to complete the management of the event. This approach is discussed hereinabove, as Feature 13.

The invention claimed is:

1. Electronic medical apparatus adapted to be implanted in a human patient, a so-called implantable medical device (IMD), which may be alternatively automatically self-controlled and remotely controlled by a medical expert, said apparatus comprising, in combination:
   (a) a first transmitting/receiving (T/R) device for transmitting medical data sensed from said patient to, and for receiving control signals from, a remote location;
   (b) an electronic medical treatment device for treating said patient in response to control signals applied thereto;
   (c) a sensor circuit, having a sensor circuit output, for producing at least one sensor circuit output signal at said sensor circuit output in response to the medical data sensed from the patient; and
   (d) a logic device coupled to each of
      (i) said sensor circuit output,
      (ii) said first T/R device, and
      (iii) said treatment device,
   for
      (i) analysis of said at least one sensor circuit output signal,
      (ii) generating a remote station notification signal,
      (iii) generating at least one local treatment device control signal, and
      (iv) generating at least one remote treatment device control signal;
   wherein:
      (1) said logic device analyzes said at least one sensor circuit output signal to detect a medical abnormality which requires notification of the medical expert at the remote location, and is operative to generate a notification signal, for consideration by said medical expert when said analysis reveals said medical abnormality;
      (2) upon receipt of said notification signal, said first T/R device transmits said notification signal representing at least one medical state of said patient to the remote location;
      (3) said logic device analyzes said at least one sensor circuit output signal to detect a medical abnormality which requires treatment and is operative to generate at least one local treatment device control signal, if required; and
      (4) said logic device is operative to generate at least one remote treatment device control signal in response to at least one remote control signal received from the remote location by said first T/R device;
      wherein said logic device determines whether to issue a notification signal, to issue a local treatment signal, to issue both a notification and a local treatment signal, or to issue neither a notification nor a local treatment signal, based on said analysis,
      whereby said IMD delivers therapy, if required, in response to one of said at least one local treatment device control signals and said at least one remote treatment device control signals.

2. The apparatus defined in claim 1, wherein said at least one remote control signal prevents said electronic medical treatment device from responding to said at least one local treatment device control signal.

3. The apparatus defined in claim 1, wherein said at least one remote control signal causes said electronic medical treatment device to administer therapy prescribed thereby.

4. The apparatus defined in claim 1, wherein
   (5) in a first operating mode said logic device generates at least one local treatment device control signal based on analysis of said at least one sensor circuit output signal;
   (6) in a second operating mode, said logic device generates at least one remote treatment device control signal in response to at least one remote control signal received from the remote location by said first T/R device; and
   (7) said logic device selects said operating mode based on at least one signal received from at least one of said first T/R device and said sensor circuit.

5. The apparatus defined in claim 4, wherein, in response to said remote control signal received from said remote location by said first T/R device said logic device selects said second operating mode.

6. The apparatus refined in claim 5, wherein said second operating mode is selected following the receipt, from said medical expert at the remote location, of at least one of:
   (a) a second operating state selecting signal; and
   (b) a remote control signal.

7. The apparatus defined in claim 4, wherein, in the absence of a signal from said first T/R device, said logic device selects said first operating mode.

8. The apparatus defined in claim 1, further comprising at least one sensor, coupled to said sensor circuit, for generating at least one electrical signal that represents a medical state of said patient.

9. The apparatus defined in claim 8, wherein said sensor is selected from the group consisting of:
   (a) a cardiac electrode for sensing cardiac electrical activity;
   (b) a device for sensing a cardiac QT interval;
   (c) a device for sensing body motion of said patient, comprising at least one of (a) an accelerometer, and (b) a piezoelectric element;
   (d) a device for sensing chest ventilation of said patient, said sensor being operable to sense at least one of (1) thoracic impedance, (2) diaphragm motion of said patient, and (3) chest wall motion of said patient;
   (e) a device for sensing spatial orientation of said patient;
   (f) a device for sensing blood oxygen saturation;
   (g) a device for sensing blood oxygen content;
   (h) a device for sensing blood carbon dioxide content;
   (i) a device for sensing blood pH;
   (j) a device for sensing blood lactic acid content;
   (k) a transducer for sensing blood pressure;
   (l) a device for sensing blood sugar;
   (m) a brain electrode for sensing brain electrical activity;
   (n) a device for sensing a concentration of a pharmacologic agent in said patient;
   (o) a device for sensing the flow rate from a circulatory heart pump;
   (p) a device for sensing the rotational speed of a heart pump motor; and
   (q) a device for sensing cardiac output.

10. The apparatus defined in claim 9, wherein said spatial orientation sensor (e) is operable to sense at least one of (i) whether a patient has fallen, and (ii) whether a patient is supine.

11. Apparatus comprising the apparatus (IMD) defined in claim 1, and further comprising a remote station at said remote location including:
   (a) a display device for displaying medical information from said patient for evaluation by said medical expert at the remote station, in response to the receipt of said at least one signal representing a medical state of the patient transmitted by the first T/R device of at least one remotely located IMD;
   (b) a first input device, responsive to said medical expert, for producing at least one remote control signal for controlling said IMD; and
   (c) a second T/R device, coupled to said display device and said input device, for electronic communication with the first T/R device of said at least one remotely located IMD; and
   wherein
   (1) said medical expert observes and analyzes said at least one signal representing a medical state of said patient via said display device, following said notification signal,
   (2) based on said analysis, said medical expert may cause said input device to generate at least one remote control signal;
   (3) said remote control signal is transmitted via said second T/R device and said first T/R device, to the logic device of said at least one remotely located IMD; and
   (4) said remote control signal causes said logic device to control said treatment device of said at least one remotely located IMD.

12. The apparatus defined in claim 11, wherein said medical expert is a human medical professional.

13. The apparatus defined in claim 11, wherein said remote control signal is a remote treatment device control signal which directs the treatment device to administer treatment.

14. The apparatus defined in claim 11, wherein
   (1) in a first operating mode said logic device generates at least one local treatment device control signal based on analysis of said at least one sensor circuit output signal;
   (2) in a second operating mode, said logic device generates at least one remote treatment device control signal in response to at least one remote control signal received from the remote location by said first T/R device; and
   (3) said logic device selects said operating mode based on at least one signal received from at least one of said first T/R device and said sensor circuit.

15. The apparatus defined in claim 14, wherein said remote control signal is a mode control signal which directs the logic device to select the operating mode.

16. The apparatus defined in claim 14, wherein said second operating mode is selected following the receipt, from said medical expert at the remote location, of at least one of:
   (a) a second operating state selecting signal; and
   (b) a remote control signal.

17. The apparatus defined in claim 11, wherein said medical expert is a medical expert logic device coupled to said second T/R device for:
   (i) receipt of said notification signal;
   (ii) receipt and analysis of said signals representing a medical state of a patient; and
   (iii) generation of medical expert logic device remote control signals;
   wherein
   (1) said medical expert logic device analyzes said at least one signal representing a medical state of said patient, following said notification signal,
   (2) based on said analysis, said medical expert logic device may generate at least one medical expert logic device remote control signal;

(3) said at least one medical expert logic device remote control signal is transmitted via said second T/R device and said first T/R device, to the logic device of said at least one IMD; and (4) said at least one medical expert logic device remote control signal causes said IMD logic device to control said treatment device of said at least one IMD.

18. The apparatus defined in claim 17, wherein i) said medical expert logic device is further coupled to a first communication device for communication with a human medical expert, ii) said medical expert logic device is operative to perform at least one of:
   a) send a human notification signal to said human medical expert;
   b) send said signals representing a medical state of a patient to said human medical expert;
   c) send said a duplicate signal representing said at least one medical expert logic device remote control signal to said human medical expert; and
   d) receive a human remote control signal;

wherein
(1) said medical expert logic device analyzes said at least one signal representing a medical state of said patient to detect a medical abnormality which requires notification of the human medical expert, and generates a human notification signal if required;

said first communication device transmits said human notification signal and at least one signal representing a medical state of said patient to said human medical expert;

(3) said medical expert logic device is operative to generate at least one first type of medical expert logic device remote control signal based on analysis of said at least one signal representing a medical state of said patient; and (4) said medical expert logic device is operative to generate at least one second type of medical expert logic device remote control signal in response to at least one human remote control signal received from said human medical expert by said communication device;

whereby said IMD delivers therapy in response to at least one of:
   i) said at least one local device treatment control signal;
   ii) said at least one first type of medical expert logic device remote control signal generated by said medical expert logic device; and
   iii) said at least one second type of medical expert logic device remote control signal, generated by said medical expert logic device in response to said at least one human control signal, generated by said human medical expert.

19. The apparatus defined in claim 18, wherein a human inhibit command from said human medical professional prevents said electronic medical treatment device from responding to at least one of (a) said at least one local treatment device control signal, and (b) said at least one first type of medical expert logic device remote control signal.

20. The apparatus defined in claim 18, wherein said at least one human remote control signal causes said electronic medical treatment device to administer therapy prescribed thereby.

21. A system comprising the apparatus defined in claim 18, and further comprising a human medical expert station at remote human location including:

(a) a display device for displaying medical information from said patient for evaluation by said human medical expert at said human medical expert station, in response to the receipt of said at least one signal representing a medical state of the patient communicated by said first communication device of said remote station;

(b) a human input device, responsive to said human medical expert, for producing at least one human remote control signal for controlling said IMD; and (c) a second communication device, coupled to said display device and said input device, for electronic communication with the first communication device of said at least one remote station; and wherein
(1) said human medical expert observes and analyzes said at least one signal representing a medical state of said patient via said display device, following said human notification signal;

(2) based on said analysis, said human medical expert may cause said human input device to generate at least one human remote control signal;

(3) said human remote control signal is transmitted via said second communication device, said first communication device, said second T/R device and said first T/R device, to the logic device of said at least one remotely located IM; and (4) said human remote control signal causes said logic device to control said treatment device of said at least one remotely located IMD.

22. The apparatus defined in claim 11, further comprising a plurality of implantable medical devices (IMDs) located at a plurality of sites remote from said remote station, wherein said medical expert at said remote station may control one or more of said plurality of IMDs following the receipt of a notification signal from one of said IMDs.

23. The apparatus defined in claim 22, wherein
(1) said logic device in each said IMD generates a unique I'D identification code for transmission with said notification signal;
(2) remote control signals are transmitted with said unique IMD identification code; and
(3) only remote control signals which are received by an IMD which contain the unique IMD identification code for that particular IMD will control that IMD;
   thereby to assure that said medical expert remote control signals control only the particular IMD for which they were intended.

24. The apparatus defined in claim 15, wherein
(1) said logic device is further operative to determine the presence and the absence of proper communication between said first T/R device and said second T/R device; and
(2) following the transmission of said notification signal,
   (i) the absence of said proper communication causes said logic device to select said first operating mode; and
   (ii) the presence of said proper communication causes said logic device to select one of said first and said second operating modes, in response to said mode control signal from said remote station.

25. The apparatus defined in claim 14, wherein
(1) said logic device is further operative to determine the presence and the absence of proper communication between said first T/R device and said second T/R device; and
(2) following the transmission of said notification signal
   (i) the absence of said proper communication causes said logic device to select said first operating mode; and (ii) the presence of said proper communication causes said logic device to select said second operating mode.

26. The apparatus defined in claim 11, wherein following the receipt of a first notification signal by said remote station, said medical expert may cause said input device to send a termination signal to said IMD, and wherein, upon receipt of said termination signal, said IMD causes cessation of transmission by said first T/R device until the occurrence of a further medical abnormality which requires a further notification of said medical expert.

27. The apparatus defined in claim 26, wherein, following the transmission of said termination signal, said logic device is further operative to analyze said at least one sensor circuit output signal to detect a further medical abnormality which requires a second notification of said medical expert at said remote location, and generates a second notification signal if required; and wherein said further medical abnormality which requires said second notification differs from said medical abnormality which requires said first notification.

28. The apparatus defined in claim 27, wherein, following said termination signal:
   (a) for a duration of time less than a re-notification time interval, said further medical abnormality causes said second notification; and
   (b) for a duration of time equal to at least said re-notification time interval, said medical abnormality causes said first notification.

29. The apparatus defined in claim 28, wherein, said logic device further comprises a clock circuit to measure said re-notification time interval.

30. The apparatus defined in claim 27, wherein
   a) said abnormality which requires a first notification is an abnormality which occurs over a first notification duration of time;
   b) said abnormality which requires said second notification is an abnormality which occurs over a second notification duration of time; and
   c) said first notification duration of time differs from said second notification duration of time.

31. The apparatus defined in claim 27, wherein
   a) said abnormality which requires a first notification is defined by a first notification frequency of abnormal medical events;
   b) said abnormality which requires said second notification is defined by a second notification frequency of abnormal medical events; and
   c) said first notification frequency differs from said second notification frequency.

32. The apparatus defined in claim 27, wherein said further abnormality which requires said second notification is defined by at least one of:
   a) a range of values of a medical parameter of said patient which is greater than a first notification value; and
   b) a range of values of a medical parameter of said patient which is less than a second notification value; and said abnormality which requires a first notification is defined by at least one of:
   a) a range of values of a medical parameter of said patient which is greater than a third notification value; and
   b) a range of values of a medical parameter of said patient which is less than a fourth notification value; and and wherein
   (i) said third notification value is greater than said first notification value; and
   (ii) said fourth notification value is less than said second notification value;
   whereby said further abnormality which requires said second notification is a less severe abnormality than said abnormality which requires a first notification.

33. The apparatus defined in claim 27, wherein said further abnormality which requires said second notification is defined by at least one of:
   a) a range of values of a medical parameter of said patient which is greater than a fifth notification value; and
   b) a range of values of a medical parameter of said patient which is less than a sixth notification value; and said abnormality which requires a first notification is defined by at least one of:
   a) a range of values of a medical parameter of said patient which is greater than a seventh notification value; and
   b) a range of values of a medical parameter of said patient which is less than an eighth notification value; and wherein
   (i) said seventh notification value is less than said fifth notification value; and
   (ii) said eighth notification value is greater than said sixth notification value;
   whereby said further abnormality which requires said second notification is a more severe abnormality than said abnormality which requires said first notification.

34. The apparatus defined in claim 27, wherein said further abnormality which requires said second notification is defined by at least one of:
   a) a range of values of a ninth function of the values of each of a fifth plurality of medical parameters of said patient which is greater than a ninth notification value; and
   b) a range of values of a ninth function of the values of each of a fifth plurality of medical parameters of said patient which is less than a tenth notification value; and and said abnormality which requires notification is defined by at least one of:
   a) a range of values of a ninth function of the values of each of a fifth plurality of medical parameters of said patient which is greater than an eleventh notification value; and
   b) a range of values of a ninth function of the values of each of a fifth plurality of medical parameters of said patient which is less than a twelfth notification value; and wherein
   (i) said eleventh notification value is greater than said ninth notification value; and
   (ii) said twelfth notification value is less than said tenth notification value.

35. The apparatus defined in claim 27, wherein said further abnormality which requires said second notification is defined by at least one of:
   a) a range of values of a tenth function of the values of each of a sixth plurality of medical parameters of said patient which is greater than a thirteenth notification value; and
   b) a range of values of a tenth function of the values of each of a sixth plurality of medical parameters of said patient which is less than a fourteenth notification value; and said abnormality which requires a first notification is defined by at least one of:
   a) a range of values of a tenth function of the values of each of a sixth plurality of medical parameters of said patient which is greater than a fifteenth notification value; and
   b) a range of values of a tenth function of the values of each of a sixth plurality of medical parameters of said patient which is less than a sixteenth notification value; and wherein (i) said fifteenth notification value is less than said thirteenth notification value; and
(ii) said sixteenth notification value is greater than said fourteenth notification value.

36. The apparatus defined in claim 27, wherein said further abnormality which requires said second notification is defined by at least one of:
a) a range of values of an eleventh function of (i) the values of each of a seventh plurality of medical parameters of said patient, and (ii) time, which is greater than a seventeenth notification value; and
b) a range of values of an eleventh function of (i) the values of each of a seventh plurality of medical parameters of said patient, and (ii) time, which is less than an eighteenth notification value;
and said abnormality which requires a first notification is defined by at least one of:
a) a range of values of an eleventh function of (i) the values of each of a seventh plurality of medical parameters of said patient, and (ii) time, which is greater than a nineteenth notification value; and
b) a range of values of an eleventh function of (i) the values of each of a seventh plurality of medical parameters of said patient, and (ii) time, which is less than a twentieth notification value;
and wherein
(i) said nineteenth notification value is greater than said seventeenth notification value; and
(ii) said twentieth, notification value is less than said eighteenth notification value.

37. The apparatus defined in claim 27, wherein said further abnormality which requires said second notification is defined by at least one of:
a) a range of values of a twelfth function of (i) the values of each of an eighth plurality of medical parameters of said patient, and (ii) time, which is greater than a twenty first notification value; and
b) a range of values of a twelfth function of (i) the values of each of an eighth plurality of medical parameters of said patient, and (ii) time, which is less than a twenty second notification value;
and said abnormality which require a first notification is defined by at least one of:
a) a range of values of a twelfth function of (i) the values of each of an eighth plurality of medical parameters of said patient, and (ii) time, which is greater than a twenty third notification value; and
b) a range of values of a twelfth function of (i) the values of each of an eighth plurality of medical parameters of said patient, and (ii) time, which is less than a twenty fourth notification value;
and wherein
(i) said twenty third notification value is less than said twenty first notification critical value; and
(ii) said twenty fourth notification value is greater than said twenty second notification critical value.

38. The apparatus defined in claim 11 wherein said medical expert may cause said input device to send a first programming signal, via said second T/R device and said first T/R device, to said logic device to change a definition of said abnormality which requires notification.

39. The apparatus defined in claim 27, wherein said medical expert may cause said input device to send a second programming signal, via said second T/R device and said first T/R device, to said logic device to change a definition of said abnormality which requires said second notification.

40. The apparatus defined in claim 28, wherein said medical expert may cause said input device to send a third programming signal, via said second T/R device and said first T/R device, to said logic device to change the duration of said re-notification time interval.

41. The apparatus defined in claim 11, wherein,
(a) said electronic medical treatment device is operative to provide a plurality of possible treatments; and
(b) following receipt of said notification signal, said medical expert may cause said input device to send a fourth programming signal, via said second T/R device and said first T/R device, to said logic device to change at least one of said plurality of possible treatments.

42. The apparatus defined in claim 41, wherein said treatment change consists of at least one of:
(a) selecting an alternate type of treatment;
(b) causing a repetitive treatment;
(c) changing a sequence of treatment steps; and
(d) changing a parameter of said treatment.

43. The apparatus defined by claim 42, wherein said parameter is selected from the group consisting of (1) a stimulating voltage, (2) a stimulating pulse width, (3) a stimulating waveform, (4) a stimulating electrical energy, (5) a rate of stimulation, (6) a choice of a stimulating electrode, (7) a flow rate of a pump, (8) a flow pressure of a pump, (9) an amount of a drug delivered by a pump, and (10) the rate of drug delivery by a pump.

44. The apparatus defined by claim 42, wherein said type of treatment is selected from the group consisting of a shock, electrical pacing, an administration a drug and a choice of a drug.

45. The apparatus defined by claim 11, wherein, following receipt of said notification signal, said medical expert may cause said input device to send a fifth programming signal, via said second T/R device and said first T/R device, to said logic device to change the criteria by which said logic device defines a medical abnormality.

46. The apparatus defined by claim 11, wherein,
(a) said logic device includes a microprocessor capable of running a plurality of algorithms for analysis of said sensor circuit output signals, and
(b) following receipt of said notification signal, said medical expert may cause said input device to send a sixth programming signal, via said second T/R device and said first T/R device, to said logic device to change the algorithm by which said logic device analyzes said at least one sensor circuit output signal.

47. The apparatus defined in claim 11, wherein said treatment device is operative to generate a treatment confirmation signal after administration of treatment to said patient, and wherein said treatment confirmation signal is transmitted to said remote station by said first T/R device.

48. The apparatus defined in claim 14, wherein, in the absence of a signal from said first T/R device, said logic device selects said first operating mode.

49. The apparatus defined in claim 11, wherein said logic device is operative to generate at least one logic device analysis signal representing a result of said analysis of said at least one sensor circuit output signal, and wherein said at least one logic device analysis signal is transmitted to said remote station by said first T/R device.

50. The apparatus defined in claim 1, wherein said at least one local treatment device control signal is transmitted to said remote station by said first T/R device.

51. The apparatus defined in claim 1, wherein
(a) said logic device is operative to analyze said at least one sensor circuit output signal to detect a medical abnormality which may require treatment; and
(b) said abnormality which requires notification is the same as said abnormality which may require treatment.

52. The apparatus defined in claim 1, wherein
(a) said logic device is operative to analyze said at least one sensor circuit output signal to detect a medical abnormality which may require treatment; and
(b) said abnormality which requires notification is different than said abnormality which may require treatment.

53. The apparatus defined in claim 52, wherein
a) said abnormality which requires notification is an abnormality which occurs over a first duration of time;
b) said abnormality which may require treatment is an abnormality which occurs over a second duration of time; and
c) said first duration of time differs from said second duration of time.

54. The apparatus defined in claim 52, wherein
a) said abnormality which requires notification is defined by a first frequency of abnormal medical events;
b) said abnormality which may require treatment is defined by a second frequency of abnormal medical events; and
c) said first frequency differs from said second frequency.

55. The apparatus defined in claim 52, wherein each said abnormality is determined based on medical data representing at least two medical parameters of said patient.

56. The apparatus defined in claim 52, wherein said abnormality which requires notification is defined by at least one of:
a) a range of values of a medical parameter of said patient which is greater than a first critical value; and
b) a range of values of a medical parameter of said patient which is less than a second critical value; and said abnormality which may require treatment is defined by at least one of:
a) a range of values of a medical parameter of said patient which is greater than a third critical value; and
b) a range of values of a medical parameter of said patient which is less than a fourth critical value; and wherein
(i) said third critical value is greater than said first critical value; and
(ii) said fourth critical value is less than said second critical value;
whereby said abnormality which requires notification is a less severe abnormality than said abnormality which may require treatment.

57. The apparatus defined in claim 52, wherein said abnormality which requires notification is defined by at least one of:
a) a range of values of a medical parameter of said patient which is greater than a fifth critical value; and
b) a range of values of a medical parameter of said patient which is less than a sixth critical value; and said abnormality which may require treatment is defined by at least one of:
a) a range of values of a medical parameter of said patient which is greater than a seventh critical value; and
b) a range of values of a medical parameter of said patient which is less than an eighth critical value; and wherein
(i) said seventh critical value is less than said fifth critical value; and
(ii) said eighth critical value is greater than said sixth critical value;
whereby said abnormality which requires notification is a more severe abnormality than said abnormality which may require treatment.

58. The apparatus defined in claim 52, wherein said abnormality which requires notification is defined by at least one of:
a) a range of values of a first function of the value of a medical parameter of said patient which is greater than a ninth critical value; and
b) a range of values of a first function of the value of a medical parameter of said patient which is less than a tenth critical value;
and said abnormality which may require treatment is defined by at least one of:
a) a range of values of a first function of the value of a medical parameter of said patient which is greater than an eleventh critical value; and
b) a range of values of a first function of the value of a medical parameter of said patient which is less than a twelfth critical value;
and wherein
(i) said eleventh critical value is greater than said ninth critical value; and
(ii) said twelfth critical value is less than said tenth critical value.

59. The apparatus defined in claim 52, wherein said abnormality which requires notification is defined by at least one of:
a) a range of values of a second function of the value of a medical parameter of said patient which is greater than a thirteenth critical value; and
b) a range of values of a second function of the value of a medical parameter of said patient which is less than a fourteenth critical value;
and said abnormality which may require treatment is defined by at least one of:
a) a range of values of a second function of the value of a medical parameter of said patient which is greater than an fifteenth critical value; and
b) a range of values of a second function of the value of a medical parameter of said patient which is less than a sixteenth critical value;
and wherein
(i) said fifteenth critical value is less than said thirteenth critical value; and
(ii) said sixteenth critical value is greater than said fourteenth critical value.

60. The apparatus defined in claim 52, wherein said abnormality which requires notification is defined by at least one of:
a) a range of values of a third function of (i) the value of a medical parameter of said patient, and (ii) time, which is greater than a seventeenth critical value; and
b) a range of values of a third function of (i) the value of a medical parameter of said patient, and (ii) time which is less than an eighteenth critical value;
and said abnormality which may require treatment is defined by at least one of:
a) a range of values of a third function of (i) the value of a medical parameter of said patient, and (ii) time, which is greater than a nineteenth critical value; and
b) a range of values of a third function of (i) the value of a medical parameter of said patient, and (ii) time, which is less than a twentieth critical value;
and wherein
(i) said nineteenth critical value is greater than said seventeenth critical value; and
(ii) said twentieth critical value is less than said eighteenth critical value.

61. The apparatus defined in claim 52, wherein said abnormality which requires notification is defined by at least one of:

a) a range of values of a fourth function of (i) the value of a medical parameter of said patient, and (ii) time, which is greater than a twenty first critical value; and
b) a range of values of a fourth function of (i) the value of a medical parameter of said patient, and (ii) time which is less than a twenty second critical value;

and said abnormality which may require treatment is defined by at least one of:
a) a range of values of a fourth function of (i) the value of a medical parameter of said patient, and (ii) time, which is greater than a twenty third critical value; and
b) a range of values of a fourth function of (i) the value of a medical parameter of said patient, and (ii) time, which is less than a twenty fourth critical value;

and wherein
(i) said twenty third critical value is less than said twenty first critical value; and
(ii) said twenty fourth critical value is greater than said twenty second critical value.

62. The apparatus defined in claim 52, wherein said abnormality which requires notification is defined by at least one of:
a) a range of values of a fifth function of the values of each of a first plurality of medical parameters of said patient which is greater than a twenty fifth critical value; and
b) a range of values of a fifth function of the values of each of a first plurality of medical parameters of said patient which is less than a twenty sixth critical value;

and said abnormality which may require treatment is defined by at least one of:
a) a range of values of a fifth function of the values of each of a first plurality of medical parameters of said patient which is greater than a twenty seventh critical value; and
b) a range of values of a fifth function of the values of each of a first plurality of medical parameters of said patient which is less than a twenty eighth critical value;

and wherein
(i) said twenty seventh critical value is greater than said twenty fifth critical value; and
(ii) said twenty eighth critical value is less than said twenty sixth critical value.

63. The apparatus defined in claim 52, wherein said abnormality which requires notification is defined by at least one of:
a) a range of values of a sixth function of the values of each of a second plurality of medical parameters of said patient which is greater than a twenty ninth critical value; and
b) a range of values of a sixth function of the values of each of a second plurality of medical parameters of said patient which is less than a thirtieth critical value;

and said abnormality which may require treatment is defined by at least one of:
a) a range of values of a sixth function of the values of each of a second plurality of medical parameters of said patient which is greater than a thirty first critical value; and
b) a range of values of a sixth function of the values of each of a second plurality of medical parameters of said patient which is less than a thirty second critical value;

and wherein
(i) said thirty first critical value is less than said twenty ninth critical value; and
(ii) said thirty second critical value is greater than said thirtieth critical value.

64. The apparatus defined in claim 52, wherein said abnormality which requires notification is defined by at least one of:
a) a range of values of a seventh function of (i) the values of each of a third plurality of medical parameters of said patient, and (ii) time, which is greater than a thirty third critical value; and
b) a range of values of a seventh function of (i) the values of each of a third plurality of medical parameters of said patient, and (ii) time, which is less than a thirty fourth critical value;

and said abnormality which may require treatment is defined by at least one of:
a) a range of values of a seventh function of (i) the values of each of a third plurality of medical parameters of said patient, and (ii) time, which is greater than a thirty fifth critical value; and
b) a range of values of a seventh function of (i) the values of each of a third plurality of medical parameters of said patient, and (ii) time, which is less than a thirty sixth critical value;

and wherein
(i) said thirty fifth critical value is greater than said thirty third critical value; and
(ii) said thirty sixth critical value is less than said thirty fourth critical value.

65. The apparatus defined in claim 52, wherein said abnormality which requires notification is defined by at least one of:
a) a range of values of an eighth function of (i) the values of each of a fourth plurality of medical parameters of said patient, and (ii) time, which is greater than a thirty seventh critical value; and
b) a range of values of an eighth function of (i) the values of each of a fourth plurality of medical parameters of said patient, and (ii) time, which is less than a thirty eighth critical value;

and said abnormality which may require treatment is defined by at least one of:
a) a range of values of an eighth function of (i) the values of each of a fourth plurality of medical parameters of said patient, and (ii) time, which is greater than a thirty ninth critical value; and
b) a range of values of an eighth function of (i) the values of each of a fourth plurality of medical parameters of said patient, and (ii) time, which is less than a fortieth critical value;

and wherein
(i) said thirty ninth critical value is less than said thirty seventh critical value; and
(ii) said fortieth critical value is greater than said thirty eighth critical value.

66. The apparatus defined in claim 1, wherein said logic device is operative to pass said at least one sensor circuit output signal to said first T/R device for transmission of said at least one sensor circuit output signal to the remote location in addition to said notification signal.

67. The apparatus defined in claim 1, wherein said sensor circuit output is further coupled to said first T/R device for transmission of said at least one sensor circuit output signal to the remote location in addition to said notification signal.

68. The apparatus defined in claim 1, further comprising a power supply coupled to a transmitter in said first T/R device, for powering said transmitter, and wherein said logic device is operable to power up said transmitter at the time a notification signal is to be sent, thereby to conserve power during periods when no transmission is required.

69. The apparatus defined in claim 68, wherein said logic device is operable to power down said transmitter upon the occurrence of an event selected from the group consisting of (i) a specified time following the last transmission, and (ii) receipt of a signal from the remote location.

70. The apparatus defined in claim 69, further comprising a supplementary power supply coupled to said treatment device, said sensor circuit, said logic device and a receiver in said first T/R device.

71. The apparatus defined in claim 11, further comprising a power supply coupled to a transmitter in said first T/R device for powering said transmitter, and wherein said transmitter is powered up in response to an activation signal received from at least one of said remote station and said logic device, thereby to conserve power during periods when no transmission is required.

72. The apparatus defined in claim 71, wherein said transmitter is powered down by at least one of:
   (a) a remote transmitter power reduction signal received from said remote station; and
   (b) a local transmitter power reduction signal received from said logic device;
thereby to reduce the power consumption when said transmitter is not in use.

73. The apparatus defined in claim 1, wherein said electronic medical treatment device is selected from the group consisting of:
   (a) a cardioverter-defibrillator device comprising:
      (i) a defibrillator circuit, having a defibrillator circuit output, for producing at least one defibrillation pulse at said defibrillator circuit output;
      (ii) at least one electrode for application of said defibrillator pulse to said patient; and
      (iii) a connecting circuit coupling said defibrillator circuit output to said at least one electrode;
   (b) a pacemaker device comprising:
      (i) a pacemaker circuit, having a pacemaker circuit output, for producing at least one pacemaker pulse at said pacemaker circuit output;
      (ii) at least one electrode for application of said pacemaker pulse to said patient; and
      (iii) a connecting circuit coupling said pacemaker circuit output to said at least one electrode;
   (a) a carotid receptor stimulator;
   (d) a brain stimulator;
   (e) a nerve stimulator;
   (f) a muscle stimulator;
   (g) a drug infusion pump; and
   (h) a circulatory heart pump for pumping the blood of said patient.

74. The apparatus defined in claim 1, wherein said electronic medical treatment device comprises:
   (a) a defibrillator circuit, having a defibrillator circuit output, for producing at least one defibrillation pulse at said defibrillator circuit output;
   (b) a pacemaker circuit, having a pacemaker circuit output, for producing at least one pacemaker pulse at said pacemaker circuit output;
   (c) at least one electrode for application of at least one of (i) said defibrillator pulse; and (ii) said pacemaker pulse to said patient;
   (d) a first connecting circuit coupling said defibrillator circuit output to at least one said electrode; and
   (e) a second connecting circuit coupling said pacemaker circuit output to at least one said electrode.

75. The apparatus defined in claim 74, wherein at least one of said at least one electrode is selectively coupled to said defibrillator circuit output and said pacing circuit output, thereby serving as both a defibrillator electrode and a pacing electrode.

76. The apparatus defined in claim 73, wherein said nerve stimulator is operative to stimulate at least one of:
   (1) at least one branch of the vagus nerve; and
   (2) at least one nerve which conveys nerve signals from a carotid artery baroreceptor.

77. The apparatus defined in claim 73, wherein said drug infusion pump is selected from the group consisting of:
   (i) a pump which supplies insulin;
   (ii) a pump which supplies a chemotherapeutic agent;
   (iii) a pump which supplies an antibiotic;
   (iv) a pump which supplies an anesthetic agent; and
   (v) a pump which supplies an analgesic agent, to said patient.

78. The apparatus defined in claim 11, wherein the IMD comprises a data storage device, coupled to said logic device, for storage of data, said data including at least one of:
   (a) medical data received from said sensor circuit;
   (b) data representing logic device analysis of medical data
   (c) data representing logic device control signals for application to said electronic medical treatment device;
   (c) data representing notification signals for transmission to said remote station; and
   (d) data representing control signals received from said remote station.

79. The apparatus defined in claim 78, wherein said data storage device is further coupled to said sensor circuit output for storage of sensor output signal data.

80. The apparatus defined in claim 78, where said data storage device is operative to provide said stored medical data to said logic device for transmission to said remote station upon receipt of at least one of:
   (1) a command received from said remote station; and
   (2) a notification signal received from said logic device.

81. The apparatus defined in claim 11, further comprising:
   (a) at least one battery, coupled to each of said first T/R device, said medical treatment device, said sensor circuit and said logic device, for supplying electrical power thereto;
   (b) battery monitoring apparatus, coupled to said battery and to said first T/R device, for monitoring battery information selected from the group consisting of (i) battery voltage, (ii) battery current drain, (iii) battery impedance, and (iv) remaining battery energy;
   wherein said battery monitoring apparatus is operative to send said battery information to said remote station via said first T/R device.

82. The apparatus defined in claim 81, wherein said first T/R device includes a transmitting device and a receiving device and wherein said transmitting device is operative to reduce its power output in response to a first power reduction signal received by said receiving device from said remote station,
   whereby said medical expert, may cause said reduction in transmission power output of said transmitting device to conserve battery function in response to receipt of battery information indicating that battery capacity has declined below a first critical value.

83. The apparatus defined in claim 81, wherein said first T/R device includes a transmitting device and a receiving device and wherein said transmitting device is operative to switch off, in response to a second power reduction signal received by said receiving device from said remote station,
   whereby said medical expert may cause a cessation of transmission by said transmitting device in response to receipt of battery information indicating that battery capacity has declined below a second critical value.

84. The apparatus defined in claim 1, further comprising at least one battery, coupled to each of said first T/R device, said medical treatment device, said sensor circuit and said logic device, for supplying electrical power thereto;
wherein
(a) said first T/R device includes a transmitting device and a receiving device and said transmitting device is operative to reduce its power output in response to a power reduction signal from said logic device; and
(b) said logic device is operative to monitor battery information selected from the group consisting of (i) battery voltage, (ii) battery current drain, (iii) battery impedance, and (iv) remaining battery energy;
whereby said logic device causes said transmitting device to reduce power output to conserve battery function in response to battery information indicating that battery capacity has declined below a first prescribed value.

85. The apparatus defined in claim 1, further comprising at least one battery, coupled to each of said first T/R device, said medical treatment device, said sensor circuit and said logic device, for supplying electrical power thereto;
wherein
(a) said first T/R device includes a transmitting device and a receiving device and said transmitting device is operative to switch off its power output in response to a power off signal from said logic device; and
(b) said logic device is operative to monitor battery information selected from the group consisting of (i) battery voltage, (ii) battery current drain, (iii) battery impedance, and (iv) remaining battery energy;
whereby said logic device causes said transmitting device to switch off, to conserve battery function, in response to battery information indicating that battery capacity has declined below a second prescribed value.

86. The apparatus defined in claim 11, further comprising:
(a) at least one first battery, coupled to said first T/R device, for supplying power to said first T/R device;
(b) at least one second battery coupled to each of said medical treatment device, said sensor circuit and said logic device, for supplying electrical power thereto; and
(c) first battery capacity monitoring apparatus, coupled to said first battery and to said first T/R device, for monitoring first battery information selected from the group consisting of (i) first battery voltage, (ii) first battery current drain, (iii) first battery impedance, and (iv) remaining first battery energy;
wherein said first battery monitoring apparatus is operative to send said first battery information to said remote station via said first T/R device.

87. The apparatus defined in claim 86, wherein at least one of said first and second battery is rechargeable.

88. The apparatus defined in claim 86, wherein said first T/R device includes a transmitting device and a receiving device and wherein said transmitting device is operative to reduce its power output in response to a first power reduction signal received by said receiving device from said remote station,
whereby said medical exert may cause said reduction in transmission power output of said transmitting device to conserve battery function in response to receipt of battery information indicating that the first battery capacity has declined below a first critical value.

89. The apparatus defined in claim 87, wherein said first T/R device includes a transmitting device and a receiving device and wherein said transmitting device is operative to switch off, in response to a second power reduction signal received by said receiving device from said remote station,
whereby said medical expert may cause a cessation of transmission by said transmitting device in response to receipt of battery information indicating that the first battery capacity has declined below a second critical value.

90. The apparatus defined in claim 86, wherein said first battery is further coupled to each of said medical treatment device, said sensor circuit and said logic device, for selectively supplying electrical power thereto in response to a battery control signal received by said receiving device from said remote station.

91. The apparatus defined in claim 86, wherein said second battery is further coupled to said first T/R device, for selectively supplying electrical power thereto in response to a battery control signal received by said receiving device from said remote station.

92. The apparatus defined in claim 11, further comprising
(a) at least one first battery, coupled to said first T/R device, for supplying power to said first T/R device and coupled to said logic device for supplying battery information to said logic device;
(b) at least one second battery coupled to each of said medical treatment device, said sensor circuit and said logic device, for supplying electrical power thereto;
wherein said logic device is operative to monitor said first battery information selected from the group consisting of (i) first battery voltage, (ii) first battery current drain, (iii) first battery impedance, and (iv) remaining first battery energy;
wherein said logic device is operative to cause said transmitting device to reduce power output in response to first battery information indicating that first battery capacity has declined below a first critical value, thereby to conserve first battery function.

93. The apparatus defined in claim 92, wherein said first T/R device includes a transmitting device and a receiving device and wherein said transmitting device is operative to reduce its power output in response to a first power reduction signal received from said logic device,
whereby said logic device may cause said reduction in transmission power output of said transmitting device to conserve battery function in response to receipt of battery information indicating that the first battery capacity has declined below said first critical value.

94. The apparatus defined in claim 92, wherein said first T/R device includes a transmitting device and a receiving device and wherein said transmitting device is operative to switch off, in response to a second power reduction signal received from said logic device,
whereby said logic device may cause a cessation of transmission by said transmitting device in response to receipt of battery information indicating that the first battery capacity has declined below a second critical value.

95. The apparatus defined in claim 1, wherein said logic device is operative to detect faults in the operation of at least one of said first T/R device, said treatment device, said sensor circuit and said logic device itself, and to generate and send a fault detection signal to said remote location via said first T/R device upon detection of a fault.

96. The apparatus defined in claim 95, wherein said fault detection signal identifies the detected fault.

97. The apparatus defined in claim 95, further comprising at least one battery and wherein the logic device is operative to determine an unfavorable value of at least one of:

a) a battery voltage;
b) a battery impedance; and
c) a charge time
and to generate and send said fault detection signal when said unfavorable value is determined.

98. Electronic medical apparatus adapted to be implanted in a human patient, a so-called implantable medical device (IMD), which may be alternatively automatically self-controlled and remotely controlled by a medical expert, said apparatus comprising, in combination:
   (a) a first transmitting/receiving (T/R) device for transmitting medical data sensed from said patient to, and for receiving control signals from, a remote location;
   (b) an electronic medical treatment device for treating said patient in response to control signals applied thereto;
   (c) a sensor circuit, having a sensor circuit output, for producing at least one sensor output signal at said sensor circuit output in response to the medical data sensed from the patient; and (d) a logic device coupled to each of
      (i) said sensor circuit output,
      (ii) said first T/R device, and
      (iii) said treatment device,
   for
      (i) analysis of said at least one sensor circuit output signal,
      (ii) generating a remote station notification signal,
      (iii) generating at least one local treatment device control signal; and
      (iv) generating at least one remote treatment device control signal;
   wherein:
   (1) said logic device analyzes said at least one sensor circuit output signal to detect a medical abnormality which requires notification of the medical expert at the remote location, and is operative to generate a notification signal, if required;
   (2) upon receipt of said notification signal, said first T/R device transmits said notification signal signal representing a medical state of said patient to the remote location;
   (3) said logic device analyzes said at least one sensor circuit output signal to detect a medical abnormality which requires treatment and is operative, in a first operating mode, to generate at least one local treatment device control signal, if required;
   (4) said logic device is operative, in a second operating mode, to generate at least one remote treatment device control signal in response to at least one remote control signal received from the remote location by said first T/R device; and
   (5) said logic device selects said operating mode based on at least one signal received from at least one of said first T/R device and said sensor circuit.

99. A method of controlling an electronic medical apparatus adapted to be implanted in a human patient, a so-called implantable medical device (IMD), which may treat a medical condition in a patient following the detection by said device of an abnormality, which may be alternatively automatically self-controlled and remotely controlled by a medical expert at a remote location, said method comprising the steps of:
   (1) monitoring signals which contain information about at least one medical state in a patient and producing medical condition signals representative of said state;
   (2) detecting a medical abnormality which may require treatment, based on said signals;
   (3) upon detection of said medical abnormality, determining by said IMD whether said treatment is to be selected automatically by said IMD or remotely by a medical expert;
   (4) if said determination is for said IMD-selected automatic treatment, the IMD automatically selecting and administering said treatment, if treatment is warranted;
   (5) if said determination is for remote selection of treatment;
      (a) transmitting information concerning said medical abnormality to said medical expert;
      (b) receiving said information for review by a medical expert;
      (c) said medical expert selecting the treatment of said medical abnormality, if treatment is warranted,
      (d) said medical expert transmitting at least one treatment control signal to said IMD, if treatment is warranted; and
      (e) said IMD administering said medical expert-selected treatment, in response to said at least one treatment control signal.

100. The method defined in claim 99, wherein a medical abnormality which results in said automatic treatment is different than a medical abnormality which results in said remote determination of treatment.

101. The method defined in claim 100, wherein
   a) said medical abnormality which results in said remote determination of treatment is an abnormality which occurs over a first duration of time;
   b) said medical abnormality which results in said automatic treatment is an abnormality which occurs over a second duration of time; and
   c) said first duration of time differs from said second duration of time.

102. The method defined in claim 100, wherein
   a) said medical abnormality which results in said remote determination of treatment is defined by a first frequency of abnormal medical events;
   b) said medical abnormality which results in said automatic treatment is defined by a second frequency of abnormal medical events; and
   c) said first frequency differs from said second frequency.

103. The method defined in claim 100, wherein each said medical abnormality is determined based on medical data representing at least two medical parameters of said patient.

104. The method defined in claim 100, wherein said medical abnormality which results in said remote determination of treatment is defined by at least one of:
   a) a range of values of a medical parameter of said patient which is greater than a first critical value; and
   b) a range of values of a medical parameter of said patient which is less than a second critical value;
and said medical abnormality which results in said automatic treatment is defined by at least one of:
   a) a range of values of a medical parameter of said patient which is greater than a third critical value; and
   b) a range of values of a medical parameter of said patient which is less than a fourth critical value;
and wherein
   (i) said third critical value is greater than said first critical value; and
   (ii) said fourth critical value is less than said second critical value;
   whereby said medical abnormality which results in said remote determination is a less severe medical abnormality than said medical abnormality which results in said automatic treatment.

105. The method defined in claim 100, wherein said medical abnormality which results in said remote determination is defined by at least one of:
    a) a range of values of a medical parameter of said patient which is greater than a fifth critical value; and
    b) a range of values of a medical parameter of said patient which is less than a sixth critical value;
and said medical abnormality which results in said automatic treatment is defined by at least one of:
    a) a range of values of a medical parameter of said patient which is greater than a seventh critical value; and
    b) a range of values of a medical parameter of said patient which is less than an eighth critical value;
and wherein
    (i) said seventh critical value is less than said fifth critical value; and
    (ii) said eighth critical value is greater than said sixth critical value;
    whereby said medical abnormality which results in said remote determination is a more severe medical abnormality than said medical abnormality which results in said automatic treatment.

106. The method defined in claim 100, wherein said medical abnormality which results in said remote determination is defined by at least one of:
    a) a range of values of a first function of the value of a medical parameter of said patient which is greater than a ninth critical value; and
    b) a range of values of a first function of the value of a medical parameter of said patient which is less than a tenth critical value;
and said medical abnormality which results in said automatic treatment is defined by at least one of:
    a) a range of values of a first function of the value of a medical parameter of said patient which is greater than an eleventh critical value; and
    b) a range of values of a first function of the value of a medical parameter of said patient which is less than a twelfth critical value;
and wherein
    (i) said eleventh critical value is greater than said ninth critical value; and
    (ii) said twelfth critical value is less than said tenth critical value.

107. The apparatus method in claim 100, wherein said medical abnormality which results in said remote determination is defined by at least one of:
    a) a range of values of a second function of the value of a medical parameter of said patient which is greater than a thirteenth critical value; and
    b) a range of values of a second function of the value of a medical parameter of said patient which is less than a fourteenth critical value;
and said medical abnormality which results in said automatic treatment is defined by at least one of:
    a) a range of values of a second function of the value of a medical parameter of said patient which is greater than an fifteenth critical value; and
    b) a range of values of a second function of the value of a medical parameter of said patient which is less than a sixteenth critical value;
and wherein
    (i) said fifteenth critical value is less than said thirteenth critical value; and
    (ii) said sixteenth critical value is greater than said fourteenth critical value.

108. The method defined in claim 99, further comprising the step of transmitting at least one abnormality detection control signal from the remote location to the IMD to change the criteria for detection of at least one of
    (a) said medical abnormality which results in said automatic treatment; and
    (b) said medical abnormality which results in said remote determination.

109. The method defined in claim 99, wherein said medical abnormality which results in automatic treatment requires the presence of at least two abnormal conditions of said patient.

110. The method defined in claim 99, wherein
    (1) said implantable medical device is at least one of a pacemaker, a cardioverter and a defibrillator;
    (2) said medical abnormality is a heart rhythm abnormality; and
    (3) the step of administering said medical treatment includes at least one of:
        (a) applying at least one shock to the patient, and
        (b) applying at least one pacing pulse to the patient.

111. The method defined in claim 110, wherein at least one of (a) said at least one shock, and (b) said at least one pacing pulse has programmed parameters, and wherein said method further comprises the step of the medical expert transmitting at least one treatment control signal to the IMD to change the programmed parameters.

112. The method defined in claim 99, further comprising the steps of:
    (6) transmitting program control signals to the IMD from the remote location to change the criteria for detecting said medical abnormality.

113. The method defined in claim 99, further comprising the steps of:
    (6) transmitting a reminder control signal to the IMD from the remote location instructing the IMD to transmit further medical condition signals after a prescribed interval of time.

114. The method defined in claim 113, wherein the reminder control signal instructs the IMD to repeatedly transmit further medical condition signals at prescribed intervals of time.

115. The method defined in claim 114, wherein the IMD automatically ceases to transmit medical condition signals when the apparent abnormality is satisfactorily corrected.

116. The method defined in claim 99, further comprising the steps of:
    (6) transmitting to the remote location, for evaluation by the medical expert, at least one of
        (a) signals representing the automatic treatment; and
        (b) said monitoring signals.

117. A method of controlling an electronic medical apparatus adapted to be implanted in a human patient, a so-called implantable medical device (IMD), which may treat a medical condition in a patient following the detection by said device of an abnormality, which may be alternatively automatically self-controlled and remotely controlled by a medical expert at a remote location, said method comprising the steps of:
    (1) at said IMD, monitoring information about at least one medical state in a patient and producing medical condition signals representative of said medical state;
    (2) at said IMD, detecting a first apparent medical abnormality which may require treatment, based on said medical condition signals;
    (3) at said IMD, upon detection of said first apparent medical abnormality, transmitting said medical condition signals to a medical expert at a remote location;

(4) at said IMD, detecting a second apparent medical abnormality which may require treatment, based on said medical condition signals, and, upon detection of said second apparent medical abnormality generating a local treatment control signal;

(5) at said IMD, in the absence of a received remote treatment control signal, administering treatment to said patient specified by said local treatment control signal, if any;

(6) at said remote location, making a determination of whether a remote treatment is warranted based on said received medical condition signals, and;

if said remote treatment is warranted, transmitting a remote treatment control signal to the IMD from the remote location;

(7) at said IMD, determining if the treatment indicated by said remote treatment control signal is different from the treatment indicated by said local treatment control signal; and (8) at said IMD, if the treatment indicated by said remote treatment control signal is different from the treatment indicated by said local treatment control signal, administering treatment to said patient specified by said remote treatment control signals.

118. A method of controlling an electronic medical apparatus adapted to be implanted in a human patient, a so-called implantable medical device (IMD), which may treat a medical condition in a patient following the detection by said device of an abnormality, which may be alternatively automatically self-controlled and remotely controlled by a medical expert at a remote location, said method comprising the steps of:

(1) at said IMD, monitoring information about at least one medical state in a patient and producing medical condition signals representative of said medical state;

(2) at said IMD, detecting an apparent medical abnormality which may require treatment, based on said medical condition signals;

(3) at said IMD, upon detection of said apparent medical abnormality, transmitting said medical condition signals to a medical expert at a remote location;

(4) at said remote location, receiving said medical condition signals and determining whether said treatment is warranted based on said medical condition signals;

(5) at said remote location, if said treatment is warranted, determining whether said treatment is to be selected automatically by said IMD or remotely by a medical expert;

(6) if said determination is for said automatic treatment by said IMD, producing a signal at said remote location for causing said IMD to automatically administer said automatic treatment to said patient;

(7) if said determination is for remote treatment by said medical expert:
   (a) said medical expert selecting the treatment of said medical abnormality;
   (b) said medical expert transmitting at least one treatment control signal to said IMD; and
   (c) said IMD administering said medical treatment, in response to said at least one treatment control signal received from said remote location.

119. The method defined in claim 118, further comprising the steps of:

(8) monitoring further said information about said at least one medical state in said patient and producing medical condition signals representative of said medical state;

(9) transmitting said medical condition signals to said medical expert at said remote location;

(10) at said remote location, determining whether said treatment was successful;

(11) if said treatment is not successful, repeating said steps (7)-(10), until at least one of:
   (a) said treatment is successful; and
   (b) a prescribed number of said treatments has been administered.

120. The method defined in claim 118, further comprising the steps of:

(8) transmitting program control signals to the IMD from the remote location to change the criteria for at least one of:
   (a) detecting said apparent medical abnormality;
   (b) automatically selecting treatment; and
   (c) automatically administering treatment.

121. The apparatus defined in claim 1, wherein said logic device analyzes said at least one sensor circuit output signal and, based on said analysis, is operative to determine whether to issue:
   (i) a notification signal and no local treatment signal,
   (ii) a local treatment signal and no notification signal,
   (iii) both a notification signal and a local treatment signal, or (iv) neither a notification signal nor a local treatment signal.

122. The apparatus defined in claim 1, wherein said notification signal indicates the occurrence of said medical abnormality.

123. The apparatus defined in claim 1, wherein said notification signal provides information representing said at least one medical state of said patient.

* * * * *